(12) United States Patent
Recio Sanchez et al.

(10) Patent No.: US 8,354,502 B2
(45) Date of Patent: Jan. 15, 2013

(54) BIOACTIVE PEPTIDES IDENTIFIED IN ENZYMATIC HYDROLYZATES OF MILK CASEINS AND METHOD OF OBTAINING SAME

(75) Inventors: Isidra Recio Sanchez, Madrid (ES); Ana Quiros Del Bosque, Madrid (ES); Blanca Hernandez Ledesma, Madrid (ES); José Angel Gomez Ruiz, Madrid (ES); Marta Miguel Castro, Madrid (ES); Maria Lourdes Amigo Garrido, Madrid (ES); Ivan Lopez Exposito, Madrid (ES); Maria Mercedes Ramos Gonzalez, Madrid (ES); Amaya Aleixandre De Artiñano, Madrid (ES); Mar Contreras Gómez, Madrid (ES)

(73) Assignee: Consejo Superior de Investigaciones Cientificas, Madrid (ES)

( * ) Notice: Subject to any disclaimer, the term of this patent is extended or adjusted under 35 U.S.C. 154(b) by 1137 days.

(21) Appl. No.: 11/921,797

(22) PCT Filed: Jun. 8, 2006

(86) PCT No.: PCT/ES2006/070079
§ 371 (c)(1),
(2), (4) Date: Aug. 4, 2008

(87) PCT Pub. No.: WO2006/131586
PCT Pub. Date: Dec. 14, 2006

(65) Prior Publication Data
US 2010/0048464 A1 Feb. 25, 2010

(30) Foreign Application Priority Data
Jun. 8, 2005 (ES) .................... 200501373

(51) Int. Cl.
*A61K 38/16* (2006.01)
(52) U.S. Cl. ........ 530/360; 530/324; 530/326; 530/328; 530/329; 530/330; 530/331; 514/15.6; 426/61; 435/68.1
(58) Field of Classification Search ........................ None
See application file for complete search history.

(56) References Cited

U.S. PATENT DOCUMENTS

| 6,060,448 A | * | 5/2000 | Smith et al. | 514/21.3 |
| 6,465,432 B1 | * | 10/2002 | Han et al. | 514/5.5 |
| 7,309,491 B2 | * | 12/2007 | Slusarewicz et al. | 424/194.1 |

FOREIGN PATENT DOCUMENTS

| DE | 4444753 | 6/1996 |
| EP | 1 188 767 | 3/2002 |

OTHER PUBLICATIONS

Kohmura et al., Agricultural and Biological Chemistry, 1989, vol. 53, pp. 2107-2114.*
International Search Report issued Oct. 11, 2006 in the International (PCT) Application of which the present application is the U.S. National Stage.
G. Y. Bakalkin et al., "Relationship Between Primary Structure and Activity in Exorphins and Endogenous Opioid Peptides", FEBS, vol. 310, No. 1, pp. 13-16, Sep. 1992.
B. Hernandez-Ledesma et al., "Angiotensin Converting Enzyme Inhibitory Activity in Commercial Fermented Products. Formation of Peptides under Simulated Gastrointestinal Digestion", Journal of Agricultural and Food Chemistry, vol. 52, pp. 1504-1510, 2004.
M. Kohmura et al., "Inhibition of Angiotensin-Converting Enzyme by Synthetic Peptides of Human β-Casein", Agricultural and Biological Chemistry, vol. 53, No. 8, pp. 2107-2114, 1989.

* cited by examiner

*Primary Examiner* — Christopher R. Tate
*Assistant Examiner* — Roy Teller
(74) *Attorney, Agent, or Firm* — Wenderoth, Lind & Ponack, L.L.P.

(57) ABSTRACT

The invention relates to the production of bioactive products that are derived from milk proteins for the production of bioactive milk products derived from milk proteins, particularly caseins. The 16 inventive peptides can be obtained chemically, biotechnologically or by means of enzymatic treatment from proteins containing same and give rise to peptides with an antimicrobial activity, an in vitro angiotensin converter inhibitor activity and/or antihypertensive activity and/or antioxidant activity. Said nutraceutical products are suitable for use in the food and pharmaceutical industries, both in the form of a hydrolyzate or bioactive peptides.

14 Claims, 11 Drawing Sheets

Figure 1:
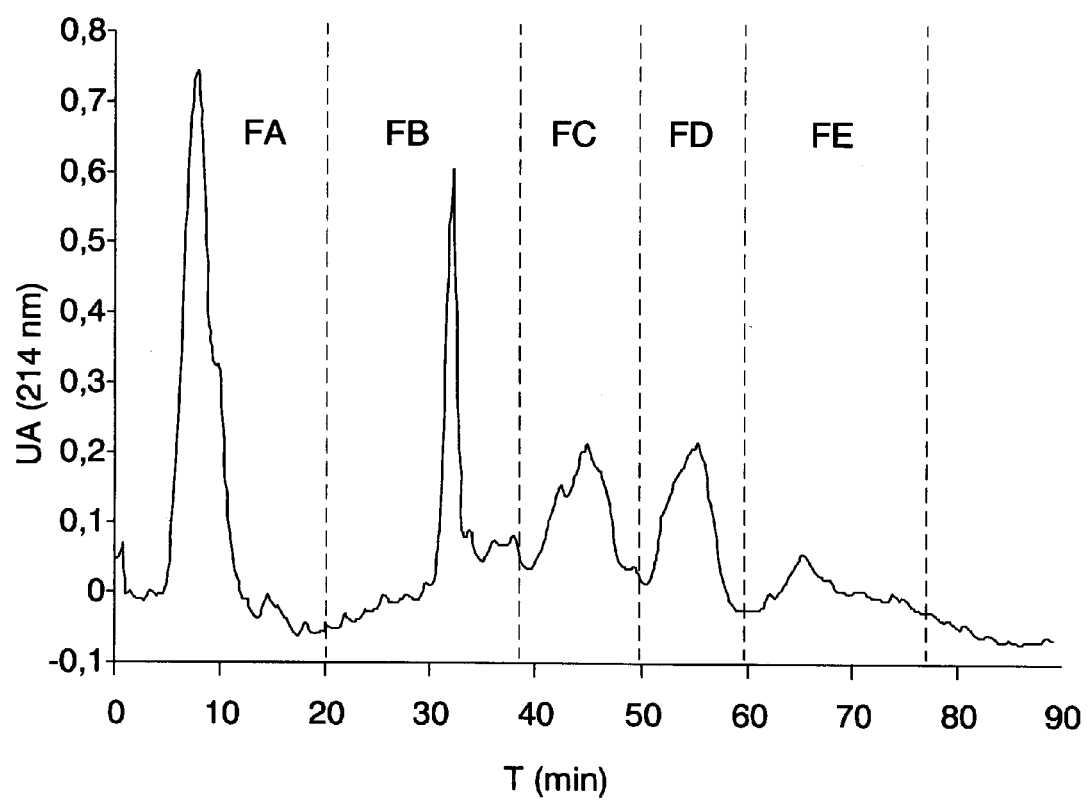

SEQUENCE LISTING

```
<160> NUMBER OF SEQ ID NOS: 17

<210> SEQ ID NO 1
<211> LENGTH: 6
<212> TYPE: PRT
<213> ORGANISM: Artificial Sequence
<220> FEATURE:
<223> OTHER INFORMATION: Derived from casein
<220> FEATURE:
<221> NAME/KEY: PEPTIDE
<222> LOCATION: (1)..(6)

<400> SEQUENCE: 1

Leu Lys Lys Ile Ser Gln
1               5

<210> SEQ ID NO 2
<211> LENGTH: 25
<212> TYPE: PRT
<213> ORGANISM: Artificial Sequence
<220> FEATURE:
<223> OTHER INFORMATION: Derived from casein
<220> FEATURE:
<221> NAME/KEY: PEPTIDE
<222> LOCATION: (20)..(25)
<223> OTHER INFORMATION: Peptide defined by SEQ. ID. NO.: 7

<400> SEQUENCE: 2

Val Asp Gln His Gln Lys Ala Met Lys Pro Trp Thr Gln Pro Lys Thr
1               5                   10                  15
```

```
Asn Ala Ile Pro Tyr Val Arg Tyr Leu
            20              25

<210> SEQ ID NO 3
<211> LENGTH: 17
<212> TYPE: PRT
<213> ORGANISM: Artificial Sequence
<220> FEATURE:
<223> OTHER INFORMATION: Derived from casein
<220> FEATURE:
<221> NAME/KEY: PEPTIDE
<222> LOCATION: (1)..(6)
<223> OTHER INFORMATION: Peptide defined by SEQ. ID. NO.: 1

<400> SEQUENCE: 3

Leu Lys Lys Ile Ser Gln Tyr Tyr Gln Lys Phe Ala Trp Pro Gln Tyr
1               5                   10                  15

Leu

<210> SEQ ID NO 4
<211> LENGTH: 16
<212> TYPE: PRT
<213> ORGANISM: Artificial Sequence
<220> FEATURE:
<223> OTHER INFORMATION: Derived from casein
<220> FEATURE:
<221> NAME/KEY: PEPTIDE
<222> LOCATION: (1)..(6)
<223> OTHER INFORMATION: Peptide defined by SEQ. ID. NO.: 1

<400> SEQUENCE: 4

Leu Lys Lys Ile Ser Gln Tyr Tyr Gln Lys Phe Ala Trp Pro Gln Tyr
1               5                   10                  15

<210> SEQ ID NO 5
<211> LENGTH: 26
<212> TYPE: PRT
<213> ORGANISM: Artificial Sequence
<220> FEATURE:
<223> OTHER INFORMATION: Derived from casein
<220> FEATURE:
<221> NAME/KEY: PEPTIDE
<222> LOCATION: (21)..(26)
<223> OTHER INFORMATION: Peptide defined by SEQ. ID. NO.: 7

<400> SEQUENCE: 5

Thr Val Asp Gln His Gln Lys Ala Met Lys Pro Trp Thr Gln Pro Lys
1               5                   10                  15

Thr Asn Ala Ile Pro Tyr Val Arg Tyr Leu
            20                  25

<210> SEQ ID NO 6
<211> LENGTH: 28
<212> TYPE: PRT
<213> ORGANISM: Artificial Sequence
<220> FEATURE:
<223> OTHER INFORMATION: Derived from casein
<220> FEATURE:
<221> NAME/KEY: PEPTIDE
<222> LOCATION: (23)..(28)
<223> OTHER INFORMATION: Peptide defined by SEQ. ID. NO.: 7

<400> SEQUENCE: 6

Leu Lys Thr Val Asp Gln His Gln Lys Ala Met Lys Pro Trp Thr Gln
1               5                   10                  15

Pro Lys Thr Asn Ala Ile Pro Tyr Val Arg Tyr Leu
            20                  25
```

```
<210> SEQ ID NO 7
<211> LENGTH: 6
<212> TYPE: PRT
<213> ORGANISM: Artificial Sequence
<220> FEATURE:
<223> OTHER INFORMATION: Derived from casein
<220> FEATURE:
<221> NAME/KEY: PEPTIDE
<222> LOCATION: (1)..(3)
<223> OTHER INFORMATION: Peptide defined by SEQ. ID. NO.: 15

<400> SEQUENCE: 7

Pro Tyr Val Arg Tyr Leu
1               5

<210> SEQ ID NO 8
<211> LENGTH: 27
<212> TYPE: PRT
<213> ORGANISM: Artificial Sequence
<220> FEATURE:
<223> OTHER INFORMATION: Derived from casein
<220> FEATURE:
<221> NAME/KEY: PEPTIDE
<222> LOCATION: (22)..(27)
<223> OTHER INFORMATION: Peptide defined by SEQ. ID. NO.: 7

<400> SEQUENCE: 8

Lys Thr Val Asp Gln His Gln Lys Ala Met Lys Pro Trp Thr Gln Pro
1               5                   10                  15

Lys Thr Asn Ala Ile Pro Tyr Val Arg Tyr Leu
            20                  25

<210> SEQ ID NO 9
<211> LENGTH: 19
<212> TYPE: PRT
<213> ORGANISM: Artificial Sequence
<220> FEATURE:
<223> OTHER INFORMATION: Derived from casein
<220> FEATURE:
<221> NAME/KEY: PEPTIDE
<222> LOCATION: (1)..(6)
<223> OTHER INFORMATION: Peptide defined by SEQ. ID. NO.: 1

<400> SEQUENCE: 9

Leu Lys Lys Ile Ser Gln Tyr Tyr Gln Lys Phe Ala Trp Pro Gln Tyr
1               5                   10                  15

Leu Lys Thr

<210> SEQ ID NO 10
<211> LENGTH: 37
<212> TYPE: PRT
<213> ORGANISM: Artificial Sequence
<220> FEATURE:
<223> OTHER INFORMATION: Derived from casein
<220> FEATURE:
<221> NAME/KEY: PEPTIDE
<222> LOCATION: (32)..(37)
<223> OTHER INFORMATION: Peptide defined by SEQ. ID. NO.: 7

<400> SEQUENCE: 10

Tyr Gln Lys Phe Ala Trp Pro Gln Tyr Leu Lys Thr Val Asp Gln His
1               5                   10                  15

Gln Lys Ala Met Lys Pro Trp Thr Gln Pro Lys Thr Asn Ala Ile Pro
            20                  25                  30

Tyr Val Arg Tyr Leu
        35

<210> SEQ ID NO 11
```

```
<211> LENGTH: 4
<212> TYPE: PRT
<213> ORGANISM: Artificial Sequence
<220> FEATURE:
<223> OTHER INFORMATION: Derived of ovine casein
<220> FEATURE:
<221> NAME/KEY: PEPTIDE
<222> LOCATION: (1)..(4)

<400> SEQUENCE: 11

Val Arg Tyr Leu
1

<210> SEQ ID NO 12
<211> LENGTH: 5
<212> TYPE: PRT
<213> ORGANISM: Artificial Sequence
<220> FEATURE:
<223> OTHER INFORMATION: Derived from casein
<220> FEATURE:
<221> NAME/KEY: PEPTIDE
<222> LOCATION: (1)..(5)

<400> SEQUENCE: 12

Arg Tyr Leu Gly Tyr
1               5

<210> SEQ ID NO 13
<211> LENGTH: 7
<212> TYPE: PRT
<213> ORGANISM: Artificial Sequence
<220> FEATURE:
<223> OTHER INFORMATION: Derived of ovine casein
<220> FEATURE:
<221> NAME/KEY: PEPTIDE
<222> LOCATION: (1)..(7)

<400> SEQUENCE: 13

Ala Tyr Phe Tyr Pro Glu Leu
1               5

<210> SEQ ID NO 14
<211> LENGTH: 7
<212> TYPE: PRT
<213> ORGANISM: Artificial sequence
<220> FEATURE:
<223> OTHER INFORMATION: Derived from casein
<220> FEATURE:
<221> NAME/KEY: PEPTIDE
<222> LOCATION: (1)..(5)
<223> OTHER INFORMATION: Peptide defined by SEQ. ID. NO.: 17

<400> SEQUENCE: 14

His Leu Pro Leu Pro Leu Leu
1               5

<210> SEQ ID NO 15
<211> LENGTH: 3
<212> TYPE: PRT
<213> ORGANISM: Artificial Sequence
<220> FEATURE:
<223> OTHER INFORMATION: Derived from casein
<220> FEATURE:
<221> NAME/KEY: PEPTIDE
<222> LOCATION: (1)..(3)

<400> SEQUENCE: 15

Pro Tyr Val
1
```

```
<210> SEQ ID NO 16
<211> LENGTH: 6
<212> TYPE: PRT
<213> ORGANISM: Artificial Sequence
<220> FEATURE:
<223> OTHER INFORMATION: Derived from casein
<220> FEATURE:
<221> NAME/KEY: PEPTIDE
<222> LOCATION: (1)..(5)
<223> OTHER INFORMATION: Peptide defined by SEQ. ID. NO.: 17

<400> SEQUENCE: 16

His Leu Pro Leu Pro Leu
1               5

<210> SEQ ID NO 17
<211> LENGTH: 5
<212> TYPE: PRT
<213> ORGANISM: Artificial Sequence
<220> FEATURE:
<223> OTHER INFORMATION: Derived from casein
<220> FEATURE:
<221> NAME/KEY: PEPTIDE
<222> LOCATION: (1)..(5)

<400> SEQUENCE: 17

His Leu Pro Leu Pro
1               5
```

BIOACTIVE PEPTIDES IDENTIFIED IN ENZYMATIC HYDROLYZATES OF MILK CASEINS AND METHOD OF OBTAINING SAME

FIELD OF APPLICATION

The invention consists of the production of bioactive products derived from milk proteins. These proteins give rise, following an enzymatic treatment, to peptides with an antimicrobial activity and/or in vitro angiotensin converter inhibitor activity (ACE-inhibitory activity) and/or antihypertensive activity and/or antioxidant activity which are suitable for use in the food and pharmaceutical industries.

STATE OF THE ART

The role of milk in human nutrition is essential from the time of birth and is a food of a high nutritional and functional value. The recent development of new biotechnological separation techniques makes it possible to fraction the different components of milk to be used for new food and non-food purposes, new applications contributing to increasing consumption thereof therefore arising. Thus, different companies devoted to the production of isolated proteins from milk fractions are interested in increasing and diversifying the uses of some components, such as the caseins and whey proteins. This is the case of the industries involved in the production of lactoferrin, used as an antimicrobial agent and which is already being used in baby food, yogurts, food supplements, special formulations, and in dental and dermatological products. Lactoferrin is also used for its antimicrobial activity as an additive in fresh milk to lengthen its shelf life.

In recent years, functional foods have broken their way into the food industry due to the heightened awareness of consumers as to the relationship that exists between diet and health. Among the functional ingredients, defined as those components which, incorporated into food, exert specific biological activities which go beyond a mere nutritional role, one of those in an outstanding position, due to their diversity and multifunctionality, being the bioactive peptides. These peptides are inactive fragments within the precursor protein, but which, following their release by means of in vivo and/or in vitro hydrolysis processes, exert different physiological functions in the body. Since their discovery in 1979, peptides derived from food proteins with different biological activities: antimicrobial, antihypertensive, immunomodulating, antithrombotic, opioid, antioxidant, etc. have been described. These peptides have a potential use in foods and/or pharmaceuticals and may be freed by means of different strategies, enzymatic hydrolysis and microbial fermentation currently being those most employed.

Some off the bioactive peptides worthy of special note are those which exert antimicrobial properties (R. Floris, I. Recio, B. Berkhout and S. Visser, Antibacterial and antiviral effects of milk proteins and derivatives thereof, Current Pharmaceutical Design, 2003, 9:1257-1275). The antimicrobial activity of milk has been studied for a long time and has conventionally been attributed to different proteins with antimicrobial activity present in this food (immunoglobulins, lactoferrin, lactoperoxidase, lysozyme, etc.) However, the antimicrobial activity of peptides derived from milk proteins has also been recently proven. Although there are no conclusive studies to date on the mechanism of action of the antimicrobial peptides derived from milk proteins, preliminary findings have described the capacity of some of these bioactive sequences to interact and smooth the bacterial membranes (D. Chapple, D. J. Mason, C. L. Joannou, E. W. Odell, V. Grant, R. W. Evans, Structure-function relationship of antibacterial synthetic peptides homologous to a helical surface region on human lactoferrin against *Escherichia coli* serotype 0111, Infection and Immunity, 1998, 66, 2434-2440). Peptides with antimicrobial activity obtained from enzymatic hydrolyzates of caseins from a bovine source, such as $\alpha_{s2}$-casein have been described (EP1114060, Process for producing cationic peptides from biological fluids) and β-casein and K-casein (WO99/26971, Antimicrobial peptides). By similar hydrolysis processes, peptides with antimicrobial properties derived from whey proteins have been isolated and identified, such as lactoferrin (WO2004/089986, Antimicrobial peptide from transferrin family).

Another group of bioactive peptides of major importance is that of the peptides having antihypertensive activity given the high incidence of coronary diseases related to hypertension in developed countries. Many of these peptides act by regulating the rennin-angiotensin system through the inhibition of the angiotensin converter enzyme (ACE) (T. Takano, Milk derived peptides and hypertension reduction, International Dairy Journal, 1998, 8: 375-381) although it is not ruled out that their effect may be by way of other mechanisms. Different peptides have been discovered that have an ACE-inhibitory activity (ACEIa) obtained from enzymatic hydrolyzates of caseins (U.S. Pat. No. 6,514,941, Method of preparing a casein hydrolyzate enriched in antihypertensive peptides) and of whey proteins (WO01/85984, Enzymatic treatment of whey proteins for the production of antihypertensive peptides, the resulting products and treatment of hypertension in mammals). Studies on the structure-activity relationship of the peptides having antihypertensive activity have revealed the fundamental role of certain hydrophobic amino acids in carrying out this activity (H.-S. Cheung, F.-L. Wang, M. A. Ondetti, E. F. Sabo and D. W. Cushman. Binding of peptide substrates and inhibitors of angiotensin-converting enzyme. Importance of the COOH-terminal dipeptide sequence. Journal of Biological Chemistry 1980, 255: 401-407). The presence of some of these amino acids has also been considered to be essential in order for the antioxidant activity to be exerted, and this activity has taken on major importance in recent years (H. M. Chen, K, Muramoto, F. Yamauchi, K. Fujimoto and K. Nokihara, Antioxidative properties of histidine-containing peptides designed from peptide fragments found in the digests of a soybean protein, Journal of Agricultural and Food Chemistry, 1998, 46: 49-53). Different degenerative diseases, such as cancer, Alzheimer's disease, cataracts or aging itself are related to the oxidation of cell components, lipids, proteins or DNA. These diseases may occur as a result of the imbalance between oxidizing agents and the antioxidant systems of the organism, for which reason the intake of antioxidant compounds in the diet could be useful in the prevention of this type of diseases. Additionally, these antioxidant compounds present in foods retard the fat oxidation processes, which are considered responsible for spoiling and for these foods taking on unpleasant odors and tastes. Recent investigations have revealed the capacity of different milk proteins and their derivatives to exert an antioxidant activity by means of different mechanisms of action. Hence, peptides have been described which have the capacity to chelate free radicals from hydrolyzated caseins (K. Suetsuna, H. Ukeda and H. Ochi, Isolation and characterization of free radical scavenging activities peptides derived from casein, Journal of Nutritional Biochemistry, 2000, 11: 128-131; EP1188767, Isolated antioxidant peptides from casein and methods for preparing, isolating and identifying antioxidant peptides) and whey proteins (B. Hernández-Ledesma, A. Dávalos, B. Bartolomé and L. Amigo, Preparation of antioxidant enzymatic hydrolyzates from α-lactalbumin and β-lactoglobulin. Identification of active peptides by HPLC-MS/MS, Journal of Agricultural and Food chemistry 2005, 53, 588-593). In addition thereto, caseins have become a major source of peptides having an inhibitory activity on the enzymes catalyzing the fat oxidation processes (S. G. Rival, S. Formaroli, C. G. Boeriu and H. J. Wichers, Caseins and casein hydrolyzates. I. Lipooxygenase inhibitory properties, Journal of Agricultural and Food Chemistry, 2001, 49: 287-294).

Most of the studies conducted to date have revolved around the biological activity of peptides derived from bovine caseins. However, there is little data published on the biological activities exerted by peptides from caseins of other types, such as ovine and caprine caseins. J. A. Gomez-Ruiz, I. Recio, and A. Pihlanto (Antimicrobial activity of ovine casein hydrolyzates. A preliminary study: Milchwissenschaft- Milk Science International 2005, 60:41-45) described the potent, dose-dependent inhibiting effect on the metabolic activity of *Escherichia coli* JM103 exerted by β-casein hydrolyzates. However, no identification was made in this study of the peptides responsible for this effect. On the contrary, several sequences released from ovine caseins during the fermentation and aging processes characteristic of Manchego cheese preparation, some of which have displayed ACE-inhibitory activity, have indeed been identified (J. A. Gómez-Ruiz, M. Ramos and I. Recio, Identification and formation of angiotensin-converting enzyme-inhibitory peptides in Manchego cheese by high-performance liquid chromatography-tandem mass spectrometry, Journal of Chromatography A, 2004, 1054: 269:277). The $IC_{50}$ values (concentration inhibiting the enzyme activity by 50%) of these sequences ranged from 24.1 to 1275.4 µM. In this study, the peptide displaying the greatest ACE-inhibiting activity was that of the $\alpha_{s1}$-casein fragment f(205-208) of sequence VRYL (SEQ. ID. No. 11), which showed a $IC_{50}$ value of 24.1 µM. (J. A. Gómez-Ruiz, M. Ramos and I. Recio, Angiotensin converting enzyme-inhibitory activity of peptides isolated from Manchego cheese. Stability under simulated gastrointestinal digestion. Int. Dairy Journal 2004, 1075-1080). There is however no data published on the capacity of these peptides to pass through the intestinal barrier and on their capacity to exert the antihypertensive effect in vivo. It must be stressed that many peptides which display in vitro ACE inhibiting activity often lose all or part of their activity when they are tested in vivo, or even peptides that do not display any major ACE-inhibitory activity in vitro do take on this activity in vivo due to the action of digestive enzymes (M. Maeno, N. Yamamoto and T. Takano, Identification of an anti-hypertensive peptide from casein hydrolysate produced by a proteinase from *Lactobacillus helveticus* CP790, Journal of Dairy Science, 1996, 79: 1316-1321). Nor are there any published studies on the multifunctional capabilities of the peptides released from the caseins of different types for exerting various biological activities, such as the antihypertensive, the antimicrobial and/or the antioxidant activity.

There are certain areas within the sequence of food proteins which, once released by hydrolysis, may display biological activities. These fragments, known as bioactive peptides, can be generated in vivo during the hydrolysis of the proteins through the action of the gastrointestinal enzymes, or in vitro through the action of specific enzymes or during the process of preparing certain foods. Given the high biological quality of milk proteins, it is of major interest to obtain bioactive peptides from these proteins, which, when taken as part of the diet, in addition to exerting their basic nutritional functions, are capable of producing metabolic or physiological effects useful in maintaining health and in preventing diseases. The production of bioactive peptides from milk proteins would make it possible to find new uses for this foodstuff beyond its conventional nutritional value, including the production of pharmaceutical and nutraceutical products. This would contribute to the development of healthy, safe, high-quality foods, contributing to making the best use of what milk products have to offer and of their being more highly valued.

DESCRIPTION OF THE INVENTION

Brief Description of the Invention

The invention consists of the production of products derived from milk proteins containing bioactive peptides having antimicrobial and/or in vitro ACE-inhibitory activity and/or antihypertensive activity and/or antioxidant activity by means of enzymatic hydrolysis of the casein fraction.

The bioactive peptides are produced by means of the hydrolysis of one or more proteins, peptides or fragments of the same which contain the sequence of amino acids of said bioactive peptides by employing proteolytic enzymes (preferably pepsin and, wherever applicable, also Corolase PP®) and hydrolysis conditions allowing the rupture of the protein chain in the appropriate places for the release thereof. In the case of using both enzymes to simulate gastrointestinal digestion, the minimal functional peptide units which would be in condition to be gastrointestinally assimilable and to pass into the bloodstream would be obtained. This property opens up the application of these peptides to other forms of administration than oral administration or increases their absorption rate. They may also be produced by means of chemical synthesis or by means of recombinant methods, etc. These peptides may be ingested as such or from raw hydrolyzates, from low molecular weight concentrates, or from other active subfractions obtained by means of size-based separation methods or chromatographic methods.

These hydrolyzates, their fractions or the peptides could form part of food products, serving as food preservatives and, upon being taken, bolstering the body's natural defenses, in addition to their also being used in the preparation of pharmaceutical products for treating disease, being particularly capable of facilitating the control of blood pressure and/or bacterial infections. The invention broadens the applications of milk proteins by contributing to making the best use of all they have to offer and to their being more highly valued.

DETAILED DESCRIPTION OF THE INVENTION

The invention provides a method for producing bioactive peptides from milk caseins. These bioactive peptides are those identified with the amino acid sequences shown in SEQ. ID No. 1, SEQ. ID No. 2, SEQ. ID No. 3, SEQ. ID No. 4, SEQ. ID No. 5, SEQ. ID No. 6, SEQ. ID No. 7, SEQ. ID No. 8, SEQ. ID No. 9, SEQ. ID No. 10, SEQ. ID No. 12, SEQ. ID No. 13, SEQ. ID No. 14, SEQ. ID No. 15, SEQ. ID No. 16, SEQ. ID No. 17, (Table 1), some of which exert antimicrobial and/or in vitro ACE-inhibitory activity and/or antihypertensive and/or antioxidant activity.

The starting material of this invention would be any appropriate substrate which were to be comprised of one or more proteins or peptides of animal or plant origins, or which come from microorganisms, which contain the amino acid sequence of the bioactive peptides of interest. Those which pertain to the $\alpha_{s2}$-casein sequence, (SEQ. ID No. 1, SEQ. ID No. 2, SEQ. ID No. 3, SEQ. ID No. 4, SEQ. ID No. 5, SEQ.

ID No. 6, SEQ. ID No. 7, SEQ. ID No. 8, SEQ. ID No. 9, SEQ. ID No. 10, Table 1), any preparation containing $\alpha_{s2}$-casein of different types, fractions thereof or peptides or fragments thereof of any size could obviously be used, either alone or in combination with other proteins. Those pertaining to $\alpha_{s1}$-casein (SEQ. ID No. 12, SEQ. ID No. 13), any preparation containing $\alpha_{s1}$-casein of different types, fractions thereof or peptides or fragments thereof of the required size could also obviously be used, either alone or in combination with other proteins, Those pertaining to β-casein ((SEQ. ID No. 14, SEQ. ID No. 16 and SEQ. ID No. 17), any preparation which contains β-casein of different types, fractions thereof, or peptides or fragments thereof of the required size could also obviously be used, either alone or in combination with other proteins. Thus, depending upon the peptide or the peptides pursued, it would be possible to use pure $\alpha_{s1}$-casein, pure $\alpha_{s2}$-casein, pure β-casein, whole casein, caseinates and milk in its different forms of presentation, fermented milk products, milk protein hydrolyzates, milk subproducts, milk derivatives for animal feed, etc.

Said starting material is dissolved or dispersed, at an appropriate concentration, in water or in a buffer solution, at a pH appropriate for the action of the proteolytic enzyme. Any proteolytic enzyme capable of breaking up the protein present in the starting material and providing the peptides of interest may be employed, but preferably pepsin at pH 2.0-3.0. Proteolytic microorganisms capable of carrying out a fermentation of the substrate and the hydrolysis of the protein could also be used.

The hydrolysis conditions: pH, temperature, enzyme-substrate ratio, interruption of the reaction, etc. are optimized for the purpose of selecting the most active hydrolyzates. In one particular embodiment, the bioactive peptides are produced by employing pepsin at pH 3.0 in an enzyme-substrate ratio of 3.7/100 (p/p) and performing the hydrolysis at 37° C. over a time period ranging from 10 minutes to 24 hours, but preferably for less than a 30-minute period.

The bioactive peptides identified as SEQ. ID No. 15, SEQ. ID. No. 17, (Table 1) which have in vitro ACE-inhibitory activity and/or antihypertensive activity, due to their structure and resistance to the gastrointestinal enzymes, would be the minimal functional peptide units which, following gastrointestinal digestion, would be in condition to be gastrointestinally assimilable and pass into the bloodstream. The starting material would be any appropriate substrate which were to be comprised of one or more proteins or peptides of animal or plant origins or which come from microorganisms which contain the sequence of amino acids of the bioactive peptides of interest (SEQ. ID No. 15, SEQ. ID. No. 17, (Table 1), preferably $\alpha_{s2}$-casein and β-casein. Any preparation containing $\alpha_{s2}$-casein or β-casein of different types, or peptides or fragments thereof of any size could obviously be used, either alone or in combination with other proteins. For example: pure $\alpha_{s2}$-casein, pure β-casein, whole casein, caseinates and milk in its different forms of presentation, fermented milk products, milk protein hydrolyzates, milk subproducts, milk derivatives for animal feed, etc.

The hydrolysis conditions: pH, temperature, enzyme-substrate ratio, interruption of the reaction, etc. are optimized for the purpose of selecting the most active hydrolyzates. In one particular embodiment, this is achieved by means of hydrolysis of the pepsin-hydrolyzed casein or of the fraction thereof of less than 3000 Da, or of the synthetic peptides which contain (PVYRYL SEQ. ID No. 7, HLPLPLL SEQ. ID. No. 14), with Corolase PP®, at pH 7-8, in an enzyme-substrate ratio 1:25 p/p at 37° C. for approximately 2.5 hours. The reaction is interrupted by heating at 95° C. for 10 minutes in a water bath. Corolase PP® is a preparation of proteolytic swine pancreas enzymes which contains amino and carboxypeptidase's in addition to trypsin and chemotrypsin.

In following, if it is desired to concentrate the bioactive peptides, and given that the peptides with antimicrobial activity are cationic in nature, the separation of the fractions containing the bioactive peptides can be performed by means of cation exchange chromatography (FPLC). From the more highly cationic fractions, active subfractions can be isolated by means of a further scan using cation exchange chromatography, hydrophobic chromatography, etc., or preferably reversed-phase high-performance liquid chromatography (RP-HPLC). Alternatively, the bioactive peptides can be concentrated from the hydrolyzate by means of methods such as ultrafiltering, dialysis, electrodialysis with the appropriate membrane pore, gel-filter chromatography, etc.

In addition to the complete hydrolyzates and the fractions thereof, the peptides shown in Table 1 marked as SEQ. ID No. 1, SEQ. ID No. 2, SEQ. ID No. 3, SEQ. ID No. 4, SEQ. ID No. 5, SEQ. ID No. 6, SEQ. ID No. 7, SEQ. ID No. 8, SEQ. ID No. 9, SEQ. ID No. 10, SEQ. ID No. 12, SEQ. ID No. 13, SEQ. ID No. 14 display bioactive properties, mainly antimicrobial activity and/or ACE-inhibitory activity and/or antihypertensive activity and/or antioxidant activity and are also an object of this invention. Specifically, the peptides identified with the sequences SEQ. ID No. 1, SEQ. ID No. 2, SEQ. ID No. 3, SEQ. ID No. 4, SEQ. ID No. 5, SEQ. ID No. 6, SEQ. ID No. 7, SEQ. ID No. 8, SEQ. ID No. 9, SEQ. ID No. 10 display antimicrobial activity Gram-positive bacteria, and at least sequence SEQ. ID. No. 3 additionally exerts a potent antimicrobial effect against *Escherichia coli*. In addition thereto, the peptides identified with sequences SEQ. ID. No. 1 and SEQ. ID. No. 7 display a potent in vitro ACE-inhibitory activity, and sequence SEQ. ID. No. 7 displays antihypertensive activity in spontaneously hypertensive rats (SHR) when administered orally to these animals. Apart from this, at least the peptide identified as SEQ. ID. No. 7 has a considerable antioxidant activity by way of an oxygen radical-chelating mechanism. Similarly, the peptide identified on the certificate of amendment as SEQ. ID. No. 14, from the β-caseins, also displays a high ACE-inhibitory activity. In addition to the pepsin-hydrolyzed casein and Corolase PP®, the peptides shown in Table 1 and marked SEQ. ID. No. 15 and SEQ. ID No. 17 have antihypertensive activity in spontaneously hypertensive rats (SHR) and are also an object of this invention. Special mention must be made of the fact that these are natural peptides from widely-consumed products from which few side effects and good tolerance may be expected.

Similarly, the bioactive peptides identified in the pepsin hydrolyzates (SEQ. ID No. 1, SEQ. ID No. 2, SEQ. ID No. 3, SEQ. ID No. 4, SEQ. ID No. 5, SEQ. ID No. 6, SEQ. ID No. 7, SEQ. ID No. 8, SEQ. ID No. 9, SEQ. ID No. 10, SEQ. ID No. 12, SEQ. ID No. 13, SEQ. ID No. 14) and, additionally, with Corolase PP®, (SEQ. ID No. 15, SEQ. ID No. 16, SEQ. ID No. 17, Table 1), on knowing the sequence thereof, currently-available technology makes it possible to obtain these by chemical and/or enzymatic peptide synthesis or by recombinant methods.

TABLE 1

Sequences of the identified bioactive peptides

| | |
|---|---|
| LKKISQ | SEQ. ID. No. 1 |
| VDQHQKAMKPWTQPKTNAIPYVRYL | SEQ. ID. No. 2 |
| LKKISQYYQKFAWPQYL | SEQ. ID. No. 3 |
| LKKISQYYQKFAWPQY | SEQ. ID. No. 4 |
| TVDQHQKAMKPWTQPKTNAIPYVRYL | SEQ. ID. No. 5 |
| LKTVDQHQKAMKPWTQPKTNAIPYVRYL | SEQ. ID. No. 6 |
| PYVRYL | SEQ. ID. No. 7 |
| KTVDQHQKAMKPWTQPKTNAIPYVRYL | SEQ. ID. No. 8 |
| LKKISQYYQKFAWPQYLKT | SEQ. ID. No. 9 |
| YQKFAWPQYLKTVDQHQKAMKPWTQPKTNAIPYVRYL | SEQ. ID. No. 10 |
| RYLGY | SEQ. ID. No. 12 |
| AYFYPBL | SEQ. ID. No. 13 |
| HLPLPLL | SEQ. ID. No. 14 |
| PYV | SEQ. ID. No. 15 |
| HLPLPL | SEQ. ID. No. 16 |
| HLPLP | SEQ. ID. No. 17 |

The production of bioactive peptides from pepsin-hydrolyzed ovine $\alpha_{s2}$-casein had not been previously described, although antimicrobial peptides derived from this protein of bovine origin had indeed been described (EP1114060, Process for producing cationic peptides from biological fluids). Some peptides derived from $\alpha_{s2}$-casein and other ovine casein in Manchego cheese with ACE-inhibitory activity had also been previously identified (J. A. Gómez-Ruiz, M. Ramos and I. Recio, Identification and formation of angiotensin-converting enzyme-inhibitory peptides in Manchego cheese by high-performance liquid chromatography-tandem mass spectrometry, Journal of Chromatography A, 2004, 1054: 269:277), although no study had been made of their in vivo antihypertensive activity. One of the peptides possessing ACE-inhibitory activity previously identified is the 205-208 fragment of ovine $\alpha_{s2}$-casein of sequence VRYL (SEQ. ID. No. 11) ($IC_{50}$ 24.1 µM). However, sequence SEQ. ID. No. 7 of this invention, PYVRYL ($IC_{50}$ 1.94) possesses an ACE-inhibitory activity 12 times more potent than the one previously described, which justifies the need of the entire sequence found in this invention in order to exert a considerable antihypertensive and/or antioxidant and/or antimicrobial activity. The entire SEQ. ID. No. 7 sequence is also required in order to exert the antihypertensive and/or antioxidant and/or antimicrobial activity. Additionally, it is also shown that, following the gastrointestinal simulation of sequence SEQ. ID. No. 7 of this invention, the minimum active fragment is that of sequence PYV SEQ. ID. No. 15.

On the other hand, this method makes it possible to obtain the bioactive peptides (SEQ. ID No. 15, SEQ. ID No. 16, SEQ. ID No. 17, Table 1) by employing enzymatic preparations and conditions simulating gastrointestinal digestion. Thus, it is probable that the fragments which are obtained will be the end products of hydrolysis, capable of being absorbed in the gastrointestinal tract and of being those directly responsible for the antihypertensive action. A further hydrolysis by the plasma peptidases cannot, however, be ruled out. The production of active small fragments is advantageous because these fragments would be easier to administer by different routes, and when administered orally, would be faster-acting.

These milk products: whole milk, milk fractions, caseins, caseinates, etc. are a cheap, readily-available substrate for producing bioactive peptides which could be used as therapeutic substances with antimicrobial activity and/or ACE-inhibitory activity and/or antihypertensive and/or antioxidant activity. These milk products can be put through a heat treatment, such as pasteurization, or alternatively be put through a drying or freeze-drying process, etc. in order to be used as functional food products, additives or food ingredients, or pharmaceutical products for the treatment and/or prevention of infections and/or arterial hypertension in all of in all forms thereof, mainly in humans, although also in animals. The quantity of hydrolyzate, low molecular weight fraction, peptides, their derivatives or pharmaceutically acceptable salts and the combinations thereof, as well as their dosage for the treatment of any disease, will vary depending on numerous factors, such as age, severity of the disease or disorder, administration route and frequency of the dose. These compounds could be presented in any administration form, solid or liquid, and be administered by any appropriate route, either oral, respiratory, rectal or topical, although they are designed particularly for oral administration in solid or liquid form.

In general, the method for producing these products: the complete hydrolyzates, the fractions thereof and their constituting peptides, can be optimized by focusing it on the production of the largest possible quantity of bioactive peptides or for controlling bitter flavor coming to bear to the extent possible, normally resulting from a high concentration of medium or low molecular weight hydrophobic peptides.

Analytical Methods

Measurement of the Antimicrobial Activity

The antimicrobial activity is determined in accordance with the method of A. Pellegrini, C. Deltting, U. Thomas, P. Hunziker (Isolation and characterization of four bactericidal domains in the bovine β-lactoglobulin Biochimica et Biophysica Acta, 2001, 1526:131-140) using as microorganisms *Escherichia coli* [American Type Culture Collection (ATCC), Rockville, Md., USA] ATCC 25922, *Listeria innocua* [Colección Española de Cultivos Tipo (CECT) Valencia, Spain] CECT 910T, *Staphylococcus epidermidis* CECT 231, *Enterococcus faecalis* CECT 795, *Serratia marcescens* CECT 854 and *Staphylococcus carnosus* CECT 4491T.

The bacterial suspensions are inoculated at 1% in the Tryptose Soy Broth (TSB) for *Escherichia coli, Serratia marcescens* and the strains of the *Staphylococcus* genus, or in the brain-heart infusion (BHI) broth for *Enterococcus faecalis* and *Listeria* innocua. The incubation is carried out at 37° C., except in the case of *Serratia marcescens*, which is at 30° C.

The bacterial innoculum, from which the work is begun, is obtained after incubating a colony grown in TSB-Agar or BHI-Agar in 10 mL of TSB or BHI overnight at 37a or 30° C. The bacterial suspension (1 mL) is diluted 1/50 with the corresponding culture medium, being incubated at the appropriate temperature for each strain up to achieving a population density of $1-4 \times 10^8$ colony-forming units (CFU) per mL. The culture is centrifuged at 2000×g for 10 minutes, the sedimented bacteria are washed twice with 15 mL phosphate buffer (pH 7.4) and the population is adjusted to $10^6$ CFU/mL. On a sterile multi-well plate (Greiner Labortechnik, Frickenhausen, Germany), 50 µL of the bacterial suspension, 50 µL of the substance to be tested and 100 µL of the phosphate buffer are mixed with 2% of the appropriate culture medium in each case, and the mixture is incubated at 37° C. or 30° C. for 2 hours. After this time, the mixture is diluted to $10^{-5}$, 100 µL of each one of the dilutions are added to TSB-Agar or BHI-Agar plates and the plates are incubated for 24 hours, after which time the colony count is taken.

The following equation is used for calculating the antimicrobial activity:

$$\text{Antimicrobial activity} = \log \frac{N_0}{N_f},$$

where $N_0$ is the starting number of $CFU/\text{mL}$ $N_f$ is the final number of $CFU/\text{mL}$ Measurement of the Angiotensin-Converting Enzyme Inhibitory Activity (ACEIa)

The ACE-inhibitory activity is measured in vitro by the method of D. W. Cushman and H. S. Cheung (Spectrophotometric assay and properties of angiotensin-converting enzyme in rabbit lung. Biochemical Pharmacology, 1971, 20:1637-1648) later modified by Y. K. Kim, S. Yoon, D. Y. Yu, B. Lönnerdal and B. H. Chung (Novel angiotensin-1-converting enzyme inhibitory peptides derived from recombinant human $\alpha_{s1}$-casein expressed in *Escherichia coli*. Journal of Dairy Research 1999, 66,431-439).

The substrate, hipuril histidil leucine (NHL, Sigma, Chemical Co, St. Louis, Mo., USA), is dissolved in 0.1 M borate buffer with 0.3 M NaCl, pH 8.3, to obtain a final concentration of 5 mM. 40 µL of each one of the samples whose ACE-inhibitory activity is to be assayed are added to 100 µL of substrate. The ACE enzyme (CE 3.4.5.1, Sigma) is added, dissolved in 50% glycerol and diluted at the point in time of performing the test in 1/10 bidistilled water. The reaction is carried out at 37° C. for 30 minutes in water bath. The enzyme is inactivated by reducing the pH with 150 µl HCL 1N. The hipuric acid formed is extracted with 1000 µL ethyl acetate. Following agitation in vortex for 20 seconds, it is centrifuged at 3000×g for 10 minutes at ambient temperature. 750 µL are taken from the organic phase that is heat-evaporated at 95° C. for 10 minutes. The hipuric acid residue is re-dissolved in 800 µL bidistilled water and, after agitating for 20 seconds, the absorbance at 228 nm is measured in a Dur-70 spectrophotometer from Beckman Instruments, Inc., Fullerton, USA.

The following equation is used for calculating the percentage of ACE-inhibitory activity:

$$\% \text{ ACE-inhibitory activity} = \frac{A control - A sample}{A control - A blank} = 100$$

The blank is used to correct the background absorbance. This blank contains substrate, enzyme and 20 µL bidistilled water instead of sample, and the reaction is halted at time zero. The control entailed one hundred percent of the enzymatic action on the substrate in absence of inhibitors and contains 20 pL of water instead of sample and is incubated for the same length of time as the sample.

The results are shown as $IC_{50}$ (µM) or concentration at which the activity of the enzyme is inhibited by 50%. The protein concentration is determined by means of the bicinchoninic acid test (Pierce-Rockord, Ill., USA), using bovine seroalbumin as a pattern.

Measurement of the Antioxidant Activity

The oxygen radical absorption capacity (ORAC) is determined by the method developed by B. X. Ou, M. Hampsch-Woodill, R L. Prior (Development and validation of an improved oxygen radical absorbance capacity assay using fluorescein as the fluorescent probe, 2001, 49:4619-4626). This method is based on the oxidation of the fluorescein by the peroxyl radicals produced in situ by thermal breakdown of the 2,2' azo-bis 2-amidinopropane dihydrochloride at $\lambda_{exo}$=493 nm and $\lambda_{cm}$=515 nm. The presence of antioxidants prevents or retards the breakdown of the fluorescein.

The fluorescein working solution is prepared daily to a concentration of 60 nM from a 100 µM fluorescein mother solution in 75 nM phosphate buffer (pH 7.5). As a control antioxidant, 6-hydroxy-2,5,7,8-tetramethylchromane-2-carboxyllic acid (Trolox) is used, which is prepared to a 20 nM concentration (mother solution) in phosphate buffer and is stored at −20° C. A Trolox calibration curve is plotted by the analysis of the pattern solutions of concentrations 12.5, 25, 40, 50 and 100 µM prepared from the mother solution. The AAPH is dissolved in the phosphate buffer to a final concentration of 143 mM, keeping it at a low temperature to prevent its breakdown.

For performing the assay, 375 µL of the sample is mixed with 375 µL AAPH and 2.225 mL fluorescein, incubating this mixture at 37° C. Every 5 minutes, the fluorescence is measured ($\lambda_{exo}$=493 nm and $\lambda_{cm}$=515 nm) in the RF-1501 fluorimeter (Shimadzu). Controls are conducted on the assay consisting of a blank containing fluorescein and phosphate buffer for checking to ensure the stability of the fluorescence during the experiment, and a positive maximum oxidation control containing fluorescein, AAPH and phosphate buffer. As a control of the maximum antioxidant activity, a 40 µM trolox solution is included in each set of samples to be analyzed. All of the samples were analyzed in triplicate.

The antioxidant activity is quantified by way of the measurement of the "area under curve" (AUC) of the fluorescein fluorescence down curve and is given in Trolox equivalents (ORAC value). The AUC is calculated using the following equation:

$$AUC=(0.5+f_5/f_0+f_{10}/f_0+f_{15}/f_0+ \ldots +f_{30}/f_0)$$

Where $f_0$ is the fluorescence at time zero and $f_0$ is the fluorescence at time "i".

The relative ORAC value for the peptides is determined using the following equation:

$$ORAC=[(AUC_{sample}-AUC_{blank})/(AUC_{trolox}-AUC_{blank})]\times\times[(trolox\ molarity/sample\ molarity]$$

Isolation of Peptide Fractions by Ion Exchange Chromatography (FPLC)

The isolation of cationic type peptide fractions is performed by the method of I. Recio, S. Visser (Identification of two distinct antibacterial domains within the sequence of bovine $\alpha_{s2}$-casein. Biochimica et Biophysica Acta 1999, 1428:314-326) with some modifications, in an FPLC system, using a HiLoad™ 26/10 SP Sepharose Fast Flow cation exchange column (Pharmacia, Uppsala, Sweden). The A and B phases are comprised of $NH_4HCO_3$ 10 nM (adjusted to pH 7.0 with HCOOH), and $NH_3$ 1.5 M, respectively. The samples are dissolved in phase A prepared to a concentration of 5 mg/mL, a volume of 5 mL being injected by means of a Superloop™ (Pharmacia) of 50 mL. The hydrolyzate elutes at a flowrate of 5 mL/min. After 20 minutes with 100% solvent A, a gradient of 0% to 50% of solvent B in A is applied in 60 minutes, followed by 20 minutes with the 50% solvent B. The detection is performed at an absorbance of 214 nm. The temperature of the column and of the mobile phases is of 9° C. The fractions are collected following several chromatography analyses.

Isolation of Peptide Fractions by Means of Reversed-Phase High-Performance Liquid Chromatography (RF-HPLC) on a Semi-Preparatory Scale.

A system comprised of two programmable pumps model Waters Delta 600, a Mod. 966 diode array detector, a Mod. 717 plus automatic injector and an automatic fraction collector (Waters Corp., Milford, Mass., USA) is used. A $C_{18}$ Prep NovaPack® HR column, 7.8×300 mm and 6 µm pore size (Waters), with a $C_{18}$ cartridge (Waters) as a column guard is used. The analyses are performed at 30° C., and the detection at 214 and 280 nm. The data acquisition is carried out with the Millennium Software version 3.2 (Waters). The $\alpha_{s2}$-casein samples are prepared at a concentration of 2.5 mg/mL and, prior to the injection, are centrifuged at 16 000×g for 10 minutes. For the elution of the samples, a binary MilliQ® water gradient (phase A) and acetonitrile (phase B) with 0.1% and 0.08% trifluoroacetic acid, are respectively used, at a flowrate of 4 mL/min. The phase B gradient is from 0% to 40% in 50 minutes and from 40% to 70% for 5 minutes, the column being washed with 70% of B for 5 minutes and reconditioning the column to the starting conditions for 25 minutes. The volume of sample injected is of 300 µL. The samples of total caseins are prepared at a concentration of 100 mg/mL and, prior to the injection, are put through a filter with a pore size of 0.45 µm. For the elution of the samples, a binary MilliQ®water gradient (phase A) and acetonitrile (phase B) with 0.1% and 0.08% trifluoroacetic acid, are respectively used, at a flowrate of 4 mL/min. The phase B gradient is from 0% to 35% in 70 minutes and from 35% to 70% for 5 minutes, the column being washed with 70% of B for 5 minutes and reconditioning the column to the starting conditions for 20 minutes. The volume of sample injected is of 50 µL.

Analysis by Tandem Mass Spectrometry (Off-Line)

An Esquire 3000 ion trap system (Bruker Daltonik GmbH, Bremen, Germany) is used. The samples are prepared to a concentration of 2 mg/mL in a 50% (v/v) water:acetonitrile solution with 0.01% formic acid (v/v). The sample is injected into the electrospray nebulizer at a flowrate of 4 µl/min using a model 22 syringe pump (Harvard Apparatus, South Natick, Mass., USA). The system uses nitrogen as nebulizing and drying gas and works at a helium pressure of $5\times10^{-3}$ bar. The mass spectrums are acquired in an interval of 100-2000 m/z at a rate of 13000 Da/second. The interpretation of the tandem mass spectrums for the identification of the peptide sequences are performed with the Biotools 2.1 program (Bruker Daltonik GmbH, Bremen, Germany)

Analysis by RP-HPLC Connected On-LINE to Tandem Mass Spectrometry (RP-HPLC-MS/MS)

An Esquire –LC system (Bruker Daltonik GmbH, Bremen, Germany) is used. The HPLC (series 1100) system is comprised of a quartenary pump, an automatic injector, an eluent degasser system and a variable wavelength ultraviolet detector. (Agilent Technologies, Waldbronn, Germany) connected on-line to an Esquire 3000 ion trap mass spectometer (Bruker Daltonik). The column is a Hi-Pore C18 column (250×4.6 mm i.d., 5 µm particle size) (Bio-Rad Laboratories, Richmond, Calif., USA). Solvent A is a mixture of water and trifluoroacetic acid (1000:0.37) and solvent B a mixture of acetonitrile and trifluoroacetic acid (1000:0.27). 50 µL of sample prepared to a concentration of 4.5 mg/ml is injected. A flowrate of 0.8 ml/min, with a linear gradient of 0% to 50% of solvent B in A in 60 minutes is used. The eluent is monitored at 214 nm by mass spectrophotometry under the same conditions as those stated in the immediately preceding section hereinabove, except for the flowrate of the injection of the sample through the nebulizer being 275 µL/min.

Study of the Antihypertensive Activity in Spontaneously Hypertensive Rats (SHR)

The effect of several of the peptides identified on the blood pressure of spontaneously hypertensive rats (SHR) is studied. The peptides are chemically synthesized for this study.

The study is conducted with male SHR rats 17-20 weeks of age weighing 300 to 350 g, from Charles River Laboratories España S. A. The rats are kept in cages, five per cage, maintaining a stable temperature of 25° C., with 12-hour light-darkness cycles, taking water and food ad libitum. Systolic blood pressure (SBP) and diastolic blood pressure (DBP) measurements are taken, for which purpose the tail cuff method is used (R. D. Bunag, Validation in awake rats of tail-cuff method for measuring systolic pressure, J. Appl. Physiol., 1973, 34: 279-282). The equipment use (Le5001, Letica) provided digital SBP and DBP values automatically. This equipment records and also facilitates the cardiac frequency of the animals. Prior to putting the tail-cuff and the transducer into place on the rats' tails, the rats are exposed to a temperature nearing 37° C. so as to facilitate the dilation of the caudal artery. Additionally, in order to assure the reliability of the measurement, the animals are accustomed to the procedure 2 weeks prior to conducting the test in question. The SBP and DBP values are determined by taking 3 consecutive measurements and calculating the average of the three values for each one of these two variables.

The spontaneously hypertensive rats (SHR) used for the study have SBP values ranging from 190 mm Hg to 220 mm Hg, and DBP values ranging from 130 mm Hg to 180 mm Hg.

The products to be tested are administered by means of an intragastric catheter within a time span ranging from 9 a.m. to 10 a.m., and the dosage tested is administered dissolved in 1 ml of distilled water. SBP and DBP readings are taken prior to the administration, and periodic measurements of these variables are also made every 2 hours following the administration, up to 8 hours post-administration. Additionally, measurements are also taken of the SBP and DBP 24 hours following the administration of the products in question. As a negative control (for establishing the circadian variation of the SBP and DBP in catheterized rats), the SBP and Dap measures taken in similar tests with rats to which 1 ml of water is administered by intragastric catheter are used. As a positive control, the SBP and DBP measurements taken in similar tests with rats to which 50 mg/kg captopril (prototype ACE-inhibitory drug) have been administered are used. This captopril dose is administered to each rat dissolved in 1 ml of distilled water.

The results are grouped and the ±average of the standard error of the measurement (SEM) for a minimum of 6 homogeneous tests is calculated. For comparing them, a one-way analysis of variance is used, followed by the Bonferroni test. The difference in values of $p<0.05$ is considered significant.

BRIEF DESCRIPTION OF WHAT IS INCLUDED IN THE FIGURES

FIG. 1: Chromatogram taken using cation exchange chromatography (FPLC) of the ovine $\alpha_{s2}$-casein pepsin-hydrolyzed for 30 minutes, in which 5 fractions (FA-FE) are selected, which were manually collected. The time, given in minutes, is plotted on the X-axis.

Figure 2A:
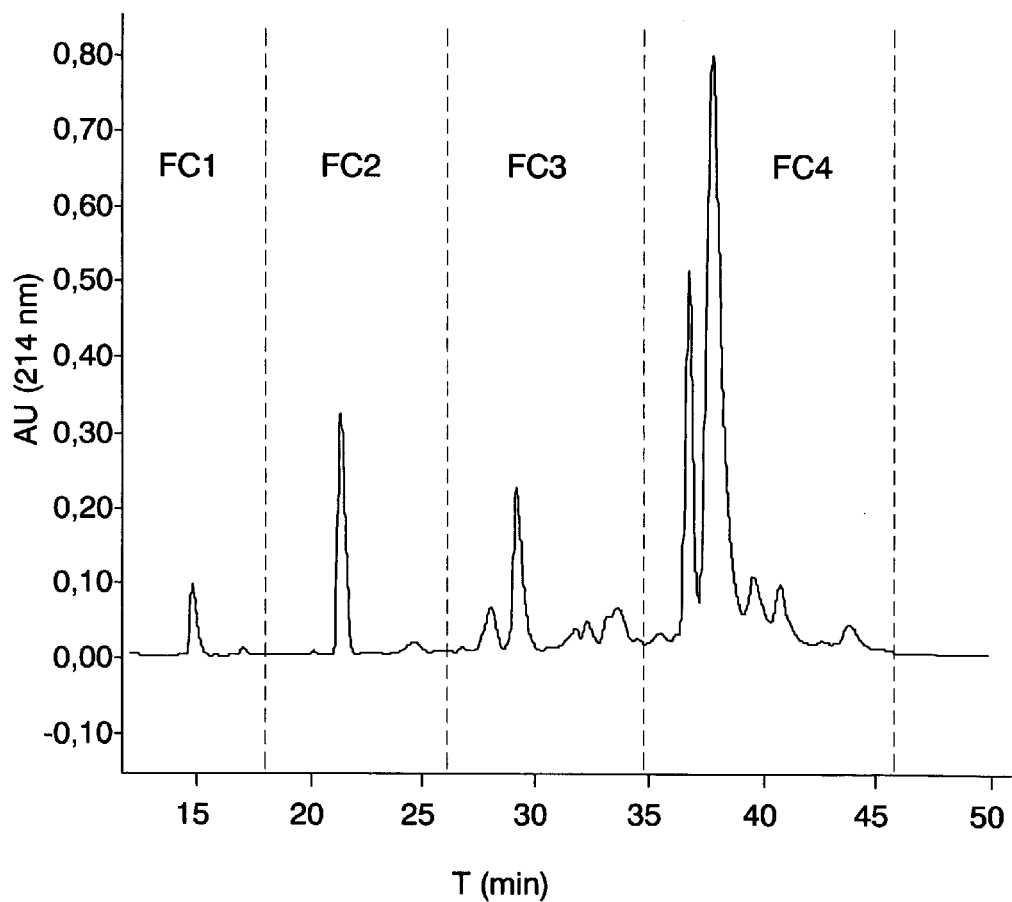

FIG. 2A: Chromatogram taken using reversed-phase high-performance liquid chromatography (RP-HPLC) on a semi-preparatory scale of the FC fraction collected from the ovine $\alpha_{s2}$-casein pepsin-hydrolyzed for 30 minutes. Four (4) sub-fractions (FC1-FC4) are selected, having been collected manually. The time, given in minutes, is plotted on the X-axis.

Figure 2B:
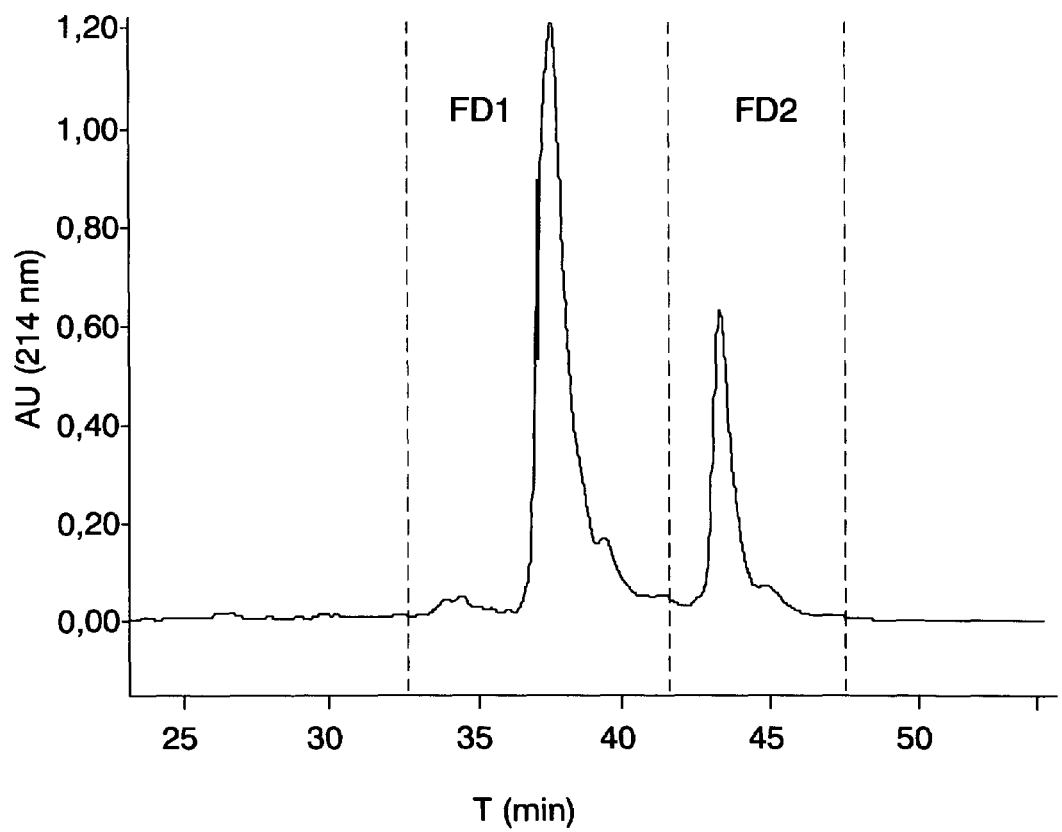

FIG. 2B: Chromatogram taken using reversed-phase high-performance liquid chromatography (RP-HPLC) on a semi-preparatory scale of the FD fraction collected from the ovine $\alpha_{s2}$-casein pepsin-hydrolyzed for 30 minutes. Two (2) sub-fractions (FD1-FD2) are selected, having been collected manually. The time, given in minutes, is plotted on the X-axis.

Figure 3:
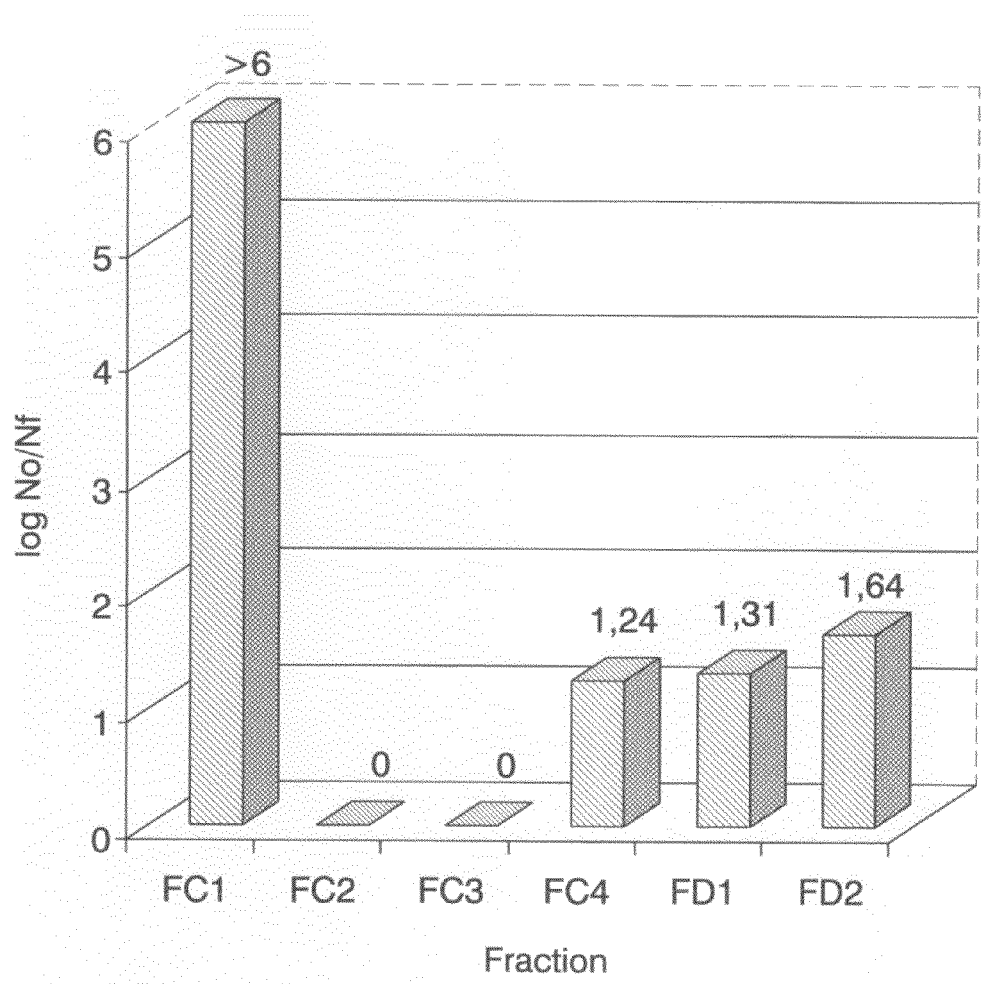

FIG. 3: Antimicrobial activity of the different subfractions obtained from the FC and FD fractions by RP-HPLC on a semi-preparatory scale.

Figure 4:
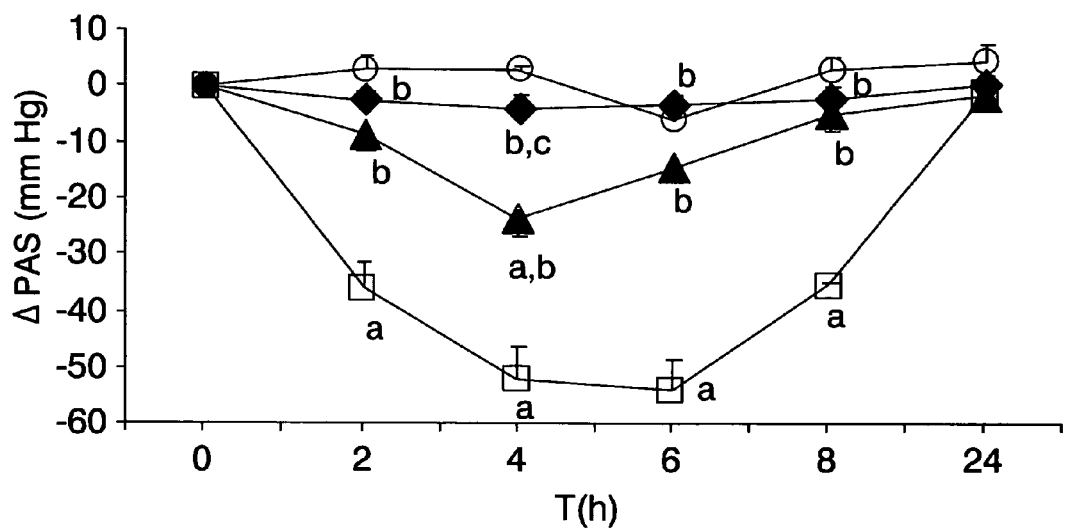
Figure 4:
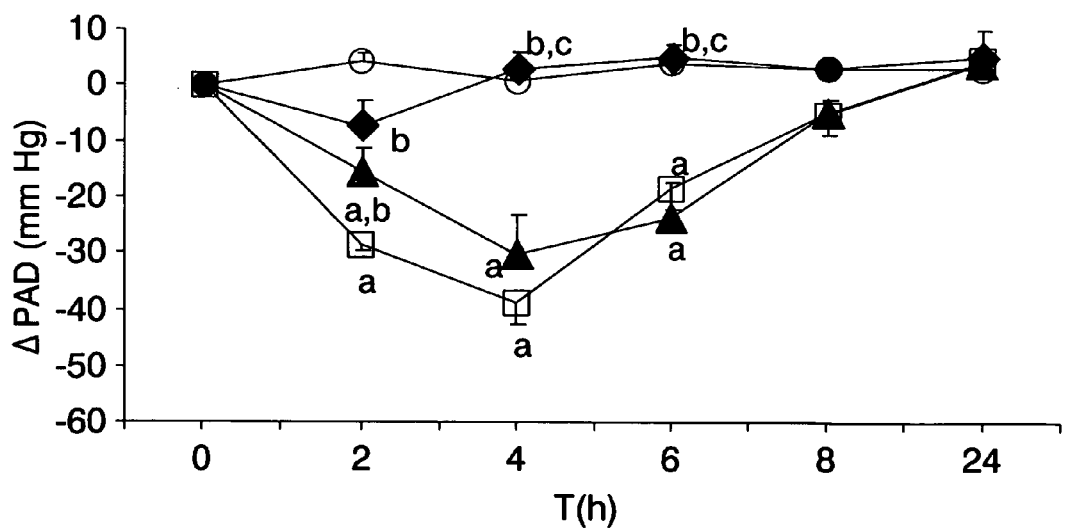

FIG. 4: Lowering of the systolic blood pressure (SBP) and the lowering of the diastolic blood pressure (DBP) found in spontaneously hypertensive rats following the administration by intragastric catheter of 1 ml of water (○), 50 mg/kg Captopril (□), 3 mg/kg PYVRYL (▲) and 3 mg/kg LKKISQ (♦). T(h) denotes the length of time having lapsed since the administration, given in hours. The data shows the ±average SEM for a minimum of 6 animals. $^{a}P<0.05$ vs water; $^{b}P<0.05$ vs Captopril; $^{b}P<0.05$ vs PYVRYL.

Figure 5:
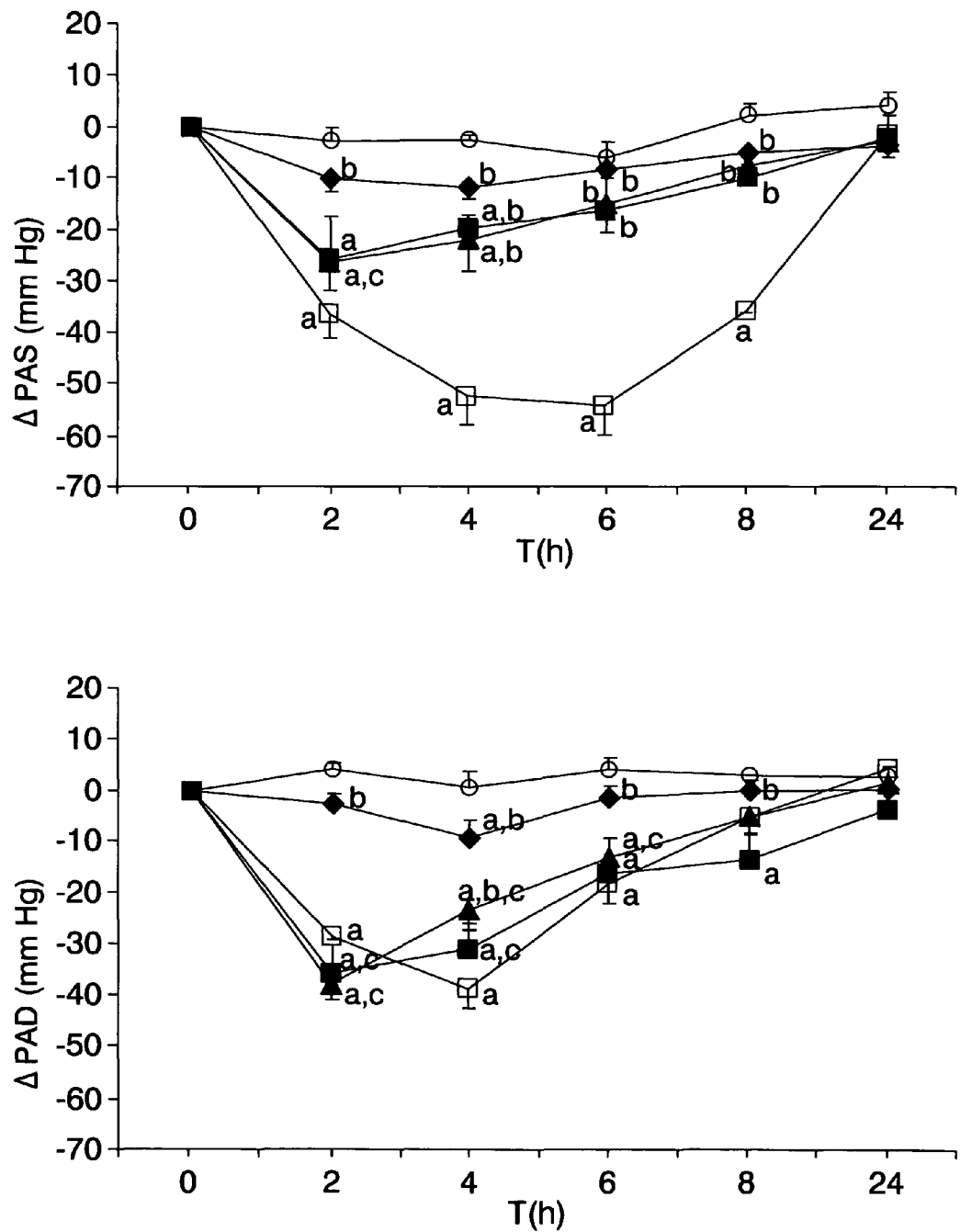

FIG. 5: Lowering of the systolic blood pressure (SBP) and the lowering of the diastolic blood pressure (DBP) found in spontaneously hypertensive rats following the administration by intragastric catheter of 1 ml of water (○), 50 mg/kg Captopril (□), 400 mg/kg casein (▲), 400 mg/kg casein hydrolyzate (♦) and 200 mg/kg F<3000 Da of the casein hydrolyzate (■). T(h) denotes the length of time having lapsed since the administration, given in hours. The data shows the ±average SEM for a minimum of 4 animals. aP<0.05 vs water; bP<0.05 vs captopril; cP<0.05 vs 400 mg/kg casein.

FIG. 6A: Chromatogram taken using reversed-phase high-performance liquid chromatography (RP-HPLC) on a semi-preparatory scale of the minor fraction of 3000 Da obtained from the casein pepsin-hydrolyzed for 3 hours. The absorbance at 214 nm is plotted on the Y-axis and the time, in minutes, on the X-axis. FIG. 6B corresponds to the angiotensin-converting enzyme inhibitory activity (ACEIa) of the chromatographic fractions obtained by RP-HPLC. Due to its potent ACE-inhibitory activity, 3 fractions were selected, which were collected automatically (F3, F5 and F6).

Figure 7:
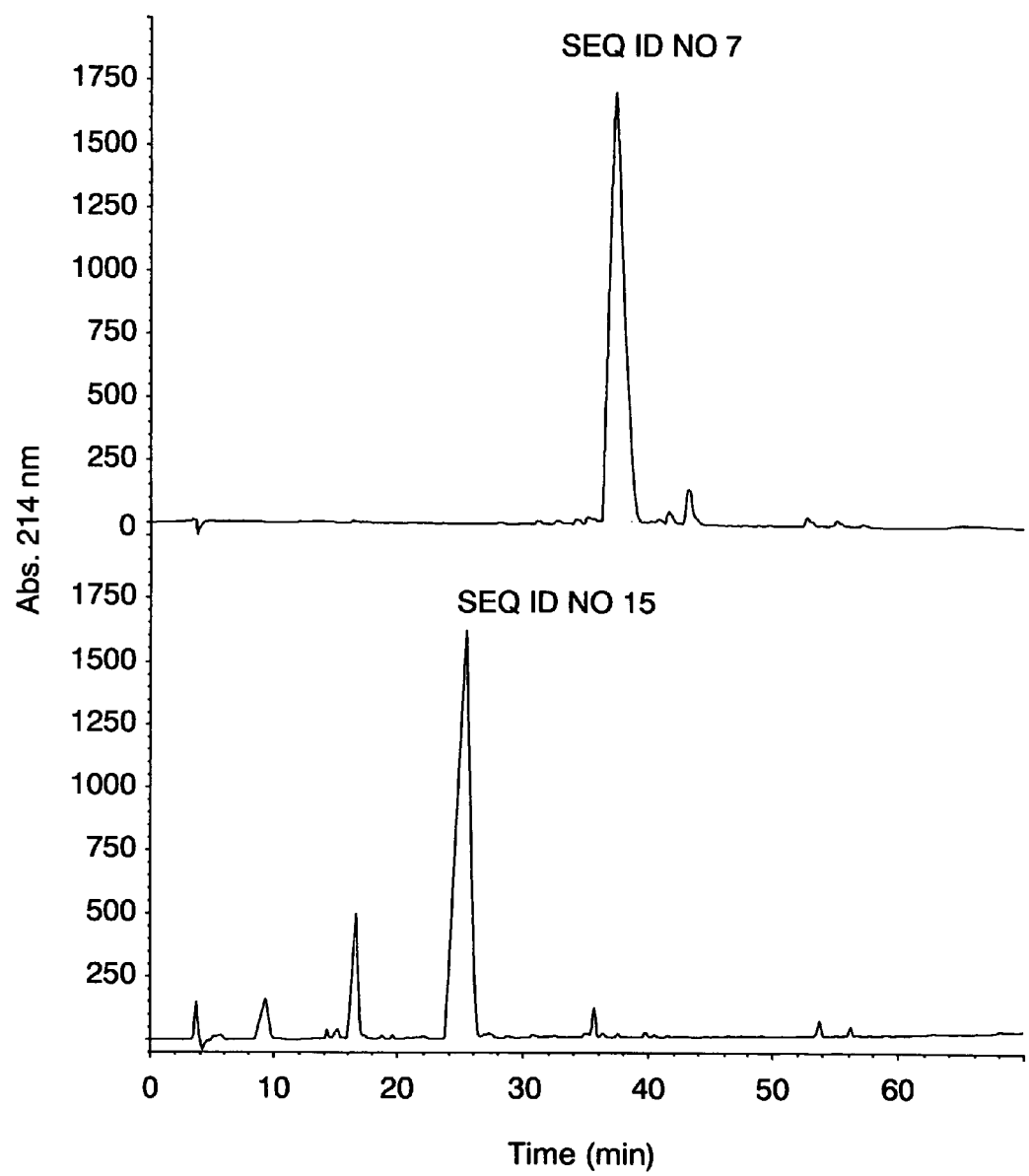

FIG. 7: Chromatogram taken using reversed-phase high-performance liquid chromatography (RP-HPLC) of the synthetic peptide PYVRYL SEQ. ID. No. 7, before and after the sequential hydrolysis with pepsin and Corolase PP®. The absorbance at 214 nm is plotted on the Y-axis and the time, in minutes, on the X-axis.

Figure 8:
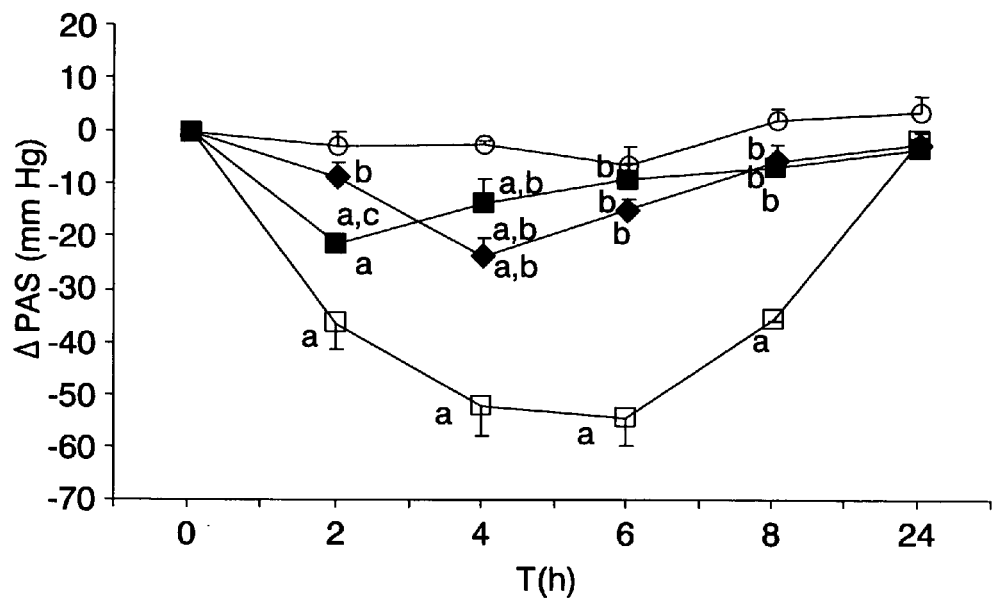
Figure 8:
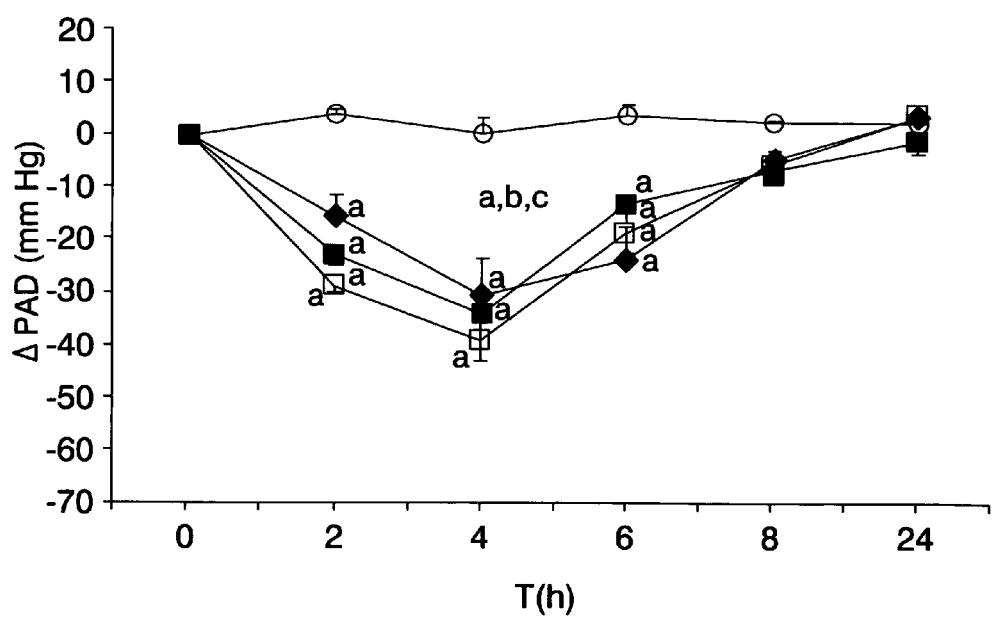

FIG. 8: Lowering of the systolic blood pressure (SBP) and the lowering of the diastolic blood pressure (DBP) found in spontaneously hypertensive rats following the administration by intragastric catheter of 1 ml of water (○), 50 mg/kg Captopril (□), 3 mg/kg PYVRYL (♦) and 2 mg/kg PYV (■). T(h) denotes the length of time having lapsed since the administration, given in hours. The data shows the average SEM for a minimum of 4 animals. aP<0.05 vs water; bP<0.05 vs captopril; cP<0.05 vs 3 mg/kg PYVRYL.

Figure 9:
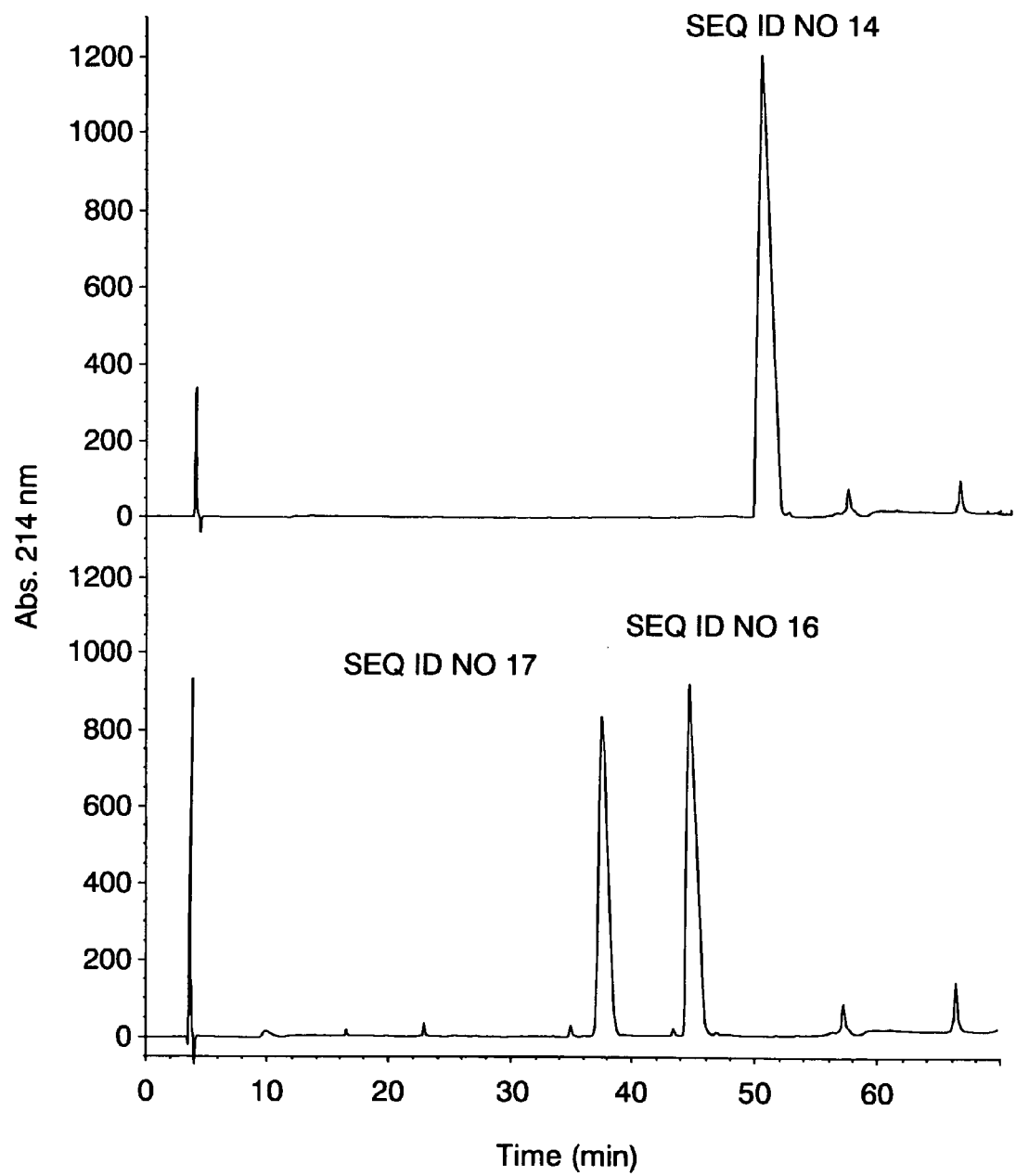

FIG. 9: Chromatogram taken using reversed-phase high-performance liquid chromatography (RP-HPLC) of the synthetic peptide HLPLPLL SEQ. ID. No. 14, before and after the sequential hydrolysis with pepsin and Corolase PP®. The absorbance at 214 nm is plotted on the Y-axis and the time, in minutes, on the X-axis.

Figure 10:
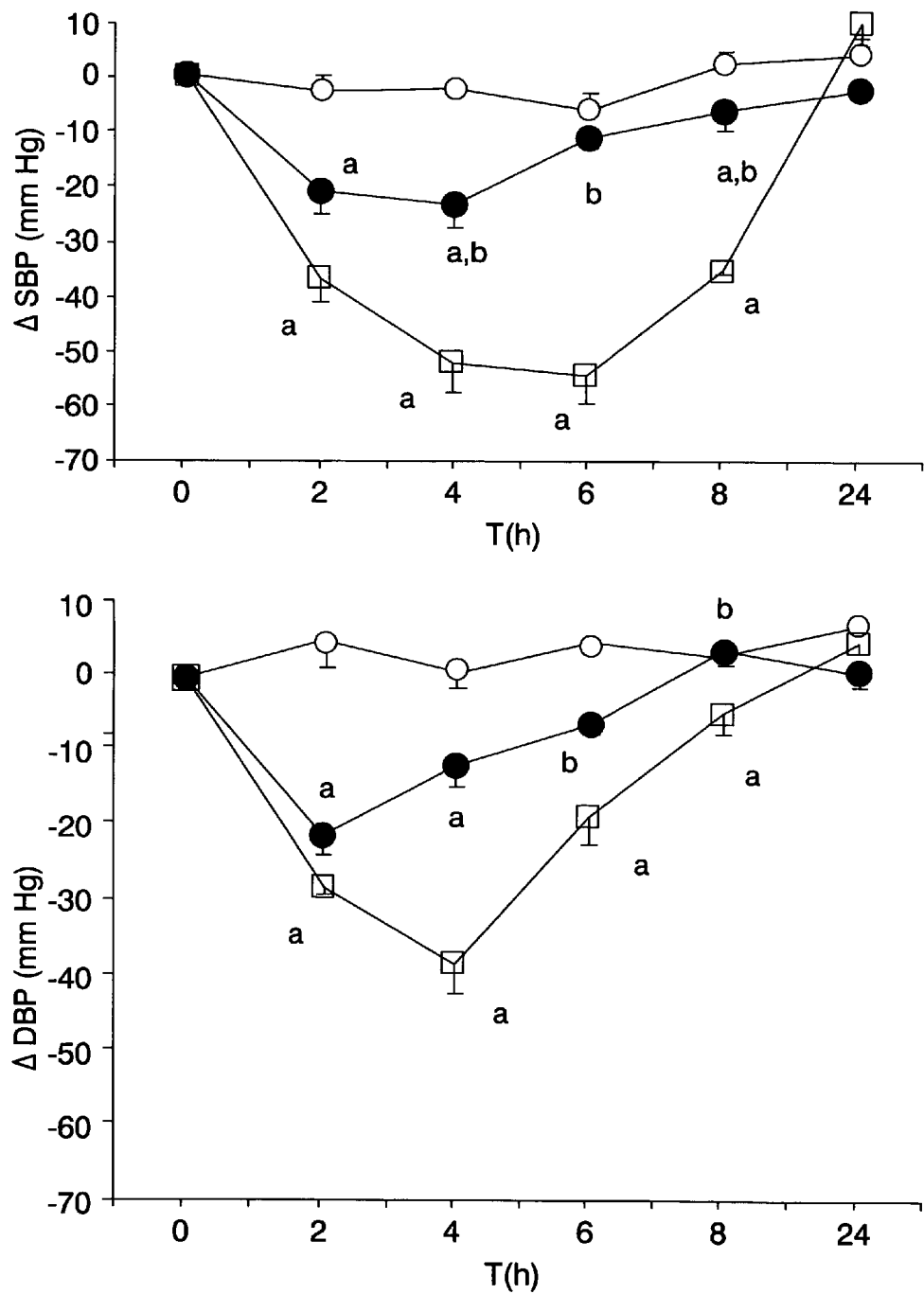

FIG. 10: Lowering of the systolic blood pressure (SBP) and the lowering of the diastolic blood pressure (DBP) obtained in spontaneously hypertensive rats following the administration by intragastric catheter of 1 ml of water (O), 50 mg/kg Captopril (□), 7 mg/kg HLPLP (•). T(h) denotes the length of time having lapsed since the administration, given in hours. The data shows the ±average SEM for a minimum of 4 animals. $^{a}P<0.05$ vs water; $^{b}P<0.05$ vs captopril.

EXAMPLES OF EMBODIMENT OF THE INVENTION

The following examples illustrate the invention, although they must not be considered as limiting the scope thereof.

Example 1

Production of Bioactive Peptides with Antimicrobial, ACE-Inhibitory, Antihypertensive and Antioxidant Activity from Pepsin-Hydrolyzed Ovine $\alpha_{s2}$-Casein The hydrolyzate was obtained by employing ovine $\alpha_{s2}$-casein as a substrate, obtained following the separation of the rest of the caseins by means of the method of H. J. Vreeman, J. A. M. van Riel (The large-scale isolation of $\alpha_{s2}$-casein from bovine casein. Netherlands Milk and Dairy Journal, 1990, 44:43-48). As an enzyme, swine pepsin was used (E.C. 3.4.23.1.570 U/mg protein) from swine stomach (Sigma Chemical, St. Louis, USA). A 0.5% aqueous solution of the ovine $\alpha_{s2}$-casein was prepared, and the pH was adjusted to 3.0 with 1 M HCl. Pepsin was added (enzyme-substrate ratio 3.7/100, p/p). The hydrolysis was carried out at 37° C. for 30 minutes. The inactivation of the pepsin was achieved by heating at 80° C. for 15 minutes and then adjusting the pH to 7.0 with 1 M NaOH. The supernatant collected following the centrifuging of the hydrolyzate at 16000 g for 15 minutes at 5° C. was analyzed by FPLC (FIG. 1), five fractions (FA-FE) having been separated, which were collected manually and then freeze-dried.

The antimicrobial activity of these five fractions was measured at a concentration of 2.5 mg/mL, using *E. coli* at 5.9×

10³ CFU/mL as the control. The results revealed that the FC and FD fractions possessed antimicrobial activity, reducing the number of microorganisms by 2.54 and 0.6 orders of magnitude, respectively.

For the purpose of identifying the peptides responsible for the antimicrobial activity, the FC and FD fractions were analyzed by RP-HPLC on a semi-preparatory scale. FIG. 2 shows the chromatographic profile of the FC fraction (FIG. 2A) and the FD fraction (FIG. 2B). Four subfractions (FC1-FC4) were separated from the FC fraction, and two subfractions (FD1-FD2) from the FD fraction. Each one of these subfractions was collected and, following the evaporation of the acetonitrile, were freeze-dried. The antimicrobial activity of these subfractions was measured at a concentration of 2.5 mg/mL, against $E.\ coli$ ($6.2\times10^6$ CFU/mL). FIG. 3 shows the antimicrobial activity values against $E.\ coli.$ of these subfractions. Of all of the subfractions, special mention must be made of FC1, which was the one which displayed greater antimicrobial activity, given that it had a bactericidal effect at the tested concentration ($\log N_f/N_o$ greater than 6). The FC4, FD1 and FD2 subfractions displayed a moderate antimicrobial activity, with values for the reduction of microorganisms of 1.24, 1.31 and 1.64 orders of magnitude, respectively.

The FC1, FC4, FD1 and FD2 subfractions were analyzed by mass spectrometry, using an ion trap analyzer following the methodology previously described. The peptides identified are shown in Table 1.

sized $\alpha_{s2}$-casein for 30 minutes (SEQ. ID. No. 1, SEQ. ID. No. 2, SEQ. ID. No. 3 and SEQ. ID. No. 7). These peptides were synthesized by the Fmoc solid-phase method, and their purity was verified by RP-HPLC-MS/MS.

The antimicrobial activity of the synthetic peptides was measured at a concentration of 0.05 mM against *Escherichia coli*, *Serratia marcescens*, *Staphylococcus carnosus*, *Staphylococcus epidermidis*, *Enterococcus faecalis* and *Listeria innocua*. The activity results are shown in Table 2.

TABLE 2

Peptides identified in subfractions FC1, FC4, FD1 and FD2 obtained from the ovine $a_{s2}$-casein pepsin-hydrolyzed for 30 minutes.

| Subfr. No. | Exp. Mass | Theor. mass | Protein | Protein Amino acids | | Sequence No. |
|---|---|---|---|---|---|---|
| FC1 | 715.4 | 715.4 | $a_{s2}$-casein | 165-170 | LKKISQ | SEQ. ID. No. 1 |
| FC4 | 3011.8 | 3011.5 | $a_{s2}$-casein | 184-208 | VDQHQKAMKPWTQPKTNAIPYVRYL | SEQ. ID. No. 2 |
| FC4 | 2203.2 | 2203.1 | $a_{s2}$-casein | 165-181 | LKKISQYYQKFAWPQYL | SEQ. ID. No. 3 |
| FC4 | 2089.8 | 2090.1 | $a_{s2}$-casein | 165-180 | LKKISQYYQKFAWPQY | SEQ. ID. No. 4 |
| FC4 | 3111.3 | 3112.6 | $a_{s2}$-casein | 183-208 | TVDQHQKAMKPWTQPKTNAIPYVRYL | SEQ. ID. No. 5 |
| FD1 | 3354.3 | 3353.8 | $a_{s2}$-casein | 181-208 | LKTVDQHQKAMKPWTQPKTNAIPYVRYL | SEQ. ID. No. 6 |
| FD1 | 809.4 | 809.4 | $a_{s2}$-casein | 203-208 | PYVRYL | SEQ. ID. No. 7 |
| FD1 | 3240.3 | 3240.7 | $a_{s2}$-casein | 182-208 | KTVDQHQKAMKPWTQPKTNAIPYVRYL | SEQ. ID. No. 8 |
| FD1 | 2433.0 | 2432.3 | $a_{s2}$-casein | 165-183 | LKKISQYYQKFAWPQYLKT | SEQ. ID. No. 9 |
| FD2 | 4566.8 | 4565.3 | $a_{s2}$-casein | 172-208 | YQKFAWPQYLKTVDQHQKAMKPWTQPKTNAIPYVRYL | SEQ. ID. No. 10 |

Example 2

Chemically Synthesized Peptides Possessing Antimicrobial Activity

The peptides mostly present in the subfractions obtained from the pepsin-hydrolyzed ovine were chemically synthe-

TABLE 3

Antimicrobial activity of the synthetic peptides identified in the subfractions FC1, FC4 and FD1 obtained from ovine $a_{s2}$-casein pepsin-hydrolyzed for 30 minutes.

| SEQ ID | Amino acids | E. coli | S. marcescens | S. carnosus | S. epidermidis | E. faecalis | L. innocua |
|---|---|---|---|---|---|---|---|
| No. 1 | LKKISQ | 0.33 | 0 | >6 | 3.6 | 0 | 1.11 |
| No. 2 | VDQHQKAMKPWTQPKTN AIPYVRYL | 0.07 | 0 | >6 | 0.61 | 0 | 1.71 |
| No. 3 | LKKISQYYQKFAWPQYL | 4.63 | 0.38 | >6 | >6 | 3.32 | >6 |
| No. 7 | PYVRYL | 0.27 | 0 | 2.23 | 2.06 | 0 | 1.13 |

These peptides display a high degree of antimicrobial activity against Gram-positive bacteria, especially against the strain tested of the *Staphylococcus* genus. Three of these peptides SEQ. ID. No. 1, SEQ. ID. No. 2 and SEQ. ID. No. 3 displayed bactericidal activity against *S. carnosus*.

However, the Gram-negative bacteria (*E. coli* and *S. marcesens*) are highly resistant to the action of all of these peptides, although special mention may be made of the fact that peptide identified as SEQ. ID. No. 3 displayed a high degree of antimicrobial activity against *E. coli*.

Example 3

Chemically Synthesized Peptides Possessing ACE-Inhibitory and Antihypertensive Activity The ACE-inhibitory activity of two of the chemically-synthesized peptides was measured, specifically sequences SEQ. ID. No. 1 and SEQ. ID. No. 7, mentioned in Example 1. The activity results, given as $IC_{50}$, or protein concentration necessary to inhibit the enzyme activity by 50%, are shown in Table 3. These two peptides display a potent ACE-inhibitory activity.

TABLE 4

ACE-inhibitory activity of the synthetic peptides identified in the FC1 and FD1 subfractions obtained from $a_{s2}$-casein pepsin-hydrolyzed for 30 minutes.

| Sequence No. | Amino acids | $CI_{50}$ |
|---|---|---|
| SEQ. ID. No. 1 | LKKISQ | 2.10 |
| SEQ. ID. No. 7 | PYVRYL | 1.94 |

The antihypertensive activity of the SEQ. ID. No. 1 and SEQ. ID. No. 7 peptides was tested, for which purpose, these peptides (3 mg/kg) were administered to spontaneously hypertensive rats (SHR). The peptides were dissolved in distilled water, and the corresponding dose was administered to each rat in a volume of 1 ml.

FIG. 4. shows the degrees to which the SBP and DBP were lowered in spontaneously hypertensive rats (SHR) at different points in time following the administration of 3 mg/kg of the SEQ. ID. No. 1 and SEQ. ID. No. 7 peptides. The administration of the SEQ. ID. No. 7 peptide can be seen as causing a significant lowering of the SBP and of the DBP in these animals. The lowering of these variables reaches its peak at 4 hours following the administration of this peptide. This lowering also displays a course over time similar to that of the SBP and DBP lowering caused by the administration of Captopril, which is a compound of proven antihypertensive activity. These results show the peptide identified by the sequence SEQ. ID. No. 7 to have a clear, marked antihypertensive effect when administered orally on an acute basis.

Example 4

Chemically Synthesized Peptides which Possess Antioxidant Activity

The antioxidant activity of the SEQ. ID. No. 7 sequence mentioned in Example 1 was measured. The peroxyl radical chelating activity is shown in following:

$ORAC_{PYVRYL} = 1.82$ μmol Trolox equivalents/μmol peptide

The results therefore show the PYVRYL (SEQ. ID. No. 7) to possess an antioxidant activity 1.82 times greater than the activity of 1 μmol Trolox.

Example 5

Production of Bioactive Peptides Possessing ACE-Inhibitory Activity from Bovine Casein with Pepsin The hydrolyzing was achieve by employing a bovine casein substrate obtained by means of isoelectric precipitations from raw cow milk. Swine peptide was used as the enzyme (E.C. 3.4.23.1. 570 U/mg protein) from swine stomach (Sigma Chemical, St. Louis, USA). A 0.5% aqueous bovine casein solution was prepared and the pH adjusted to 2.0 with 1 M HCl. Pepsin was added (enzyme-substrate ratio 3.7/100 p/p). The hydrolysis was performed at 37° C. for 3 hours. The pepsin was inactivated by heating at 80° C. for 20 min and then adjusting the pH to 7.0 with 1M NaOH. The supernatant collected following the centrifuging of the hydrolyzate at 16000×g for 15 minutes at 5° C. was ultrafiltered through a hydrophyllic membrane with a 3000 Da pore size (Centripep, Amicon Inc, Beverly, Mass., USA). The ACE-inhibitory and antihypertensive activity was determined in SHR (according to that previously described in analytical methods) of the total hydrolyzate and of the permeate (fraction of the hydrolyzate of a molecular weight lower than 3000 Da). Table 4 shows the ACE-inhibitory activity values, given as $IC_{50}$ or protein concentration necessary for inhibiting the enzyme activity by 50%, and the protein content determined by the Kjeldahl method. FIG. 5 shows the lowering of the SBP and DBP found in spontaneously hypertensive rats (SHR) at different points in time following the administration of casein hydrolyzate and following the administration of the casein hydrolyzate fraction with a molecular weight lower than 3000 Da. As shown in the Table, the administration of casein hydrolyzate causes a significant lowering of the SBP and of the DBP in these animals. The administration of the casein hydrolyzate fraction of a molecular weight lower than 3000 Da causes the SBP and the DBP to be lowered in the spontaneously hypertensive rats to degrees similar to those observed after administering the casein hydrolyzate. The lowering of these variable reaches its peak 2 hours following the administration of these products. The administration of unhydrolyzed casein does not significantly modify the SBP of the spontaneously hypertensive rats (SHR) and lowers the DBP to a much lesser degree than the previous compounds in these animals. These results show the casein hydrolyzate and the casein hydrolyzate fraction of a molecular weight lower than 300 Da to have a clear antihypertensive effect when they are administered orally on an acute basis.

TABLE 5

ACE-inhibitory activity of the pepsin-hydrolyzed bovine caseins and of the permeate (fraction < 300 Da) and the retenate (F > 3000 Da) obtained following the ultrafiltering process.

| | $CI_{50}$ (µg/ml) | % protein (p/p) (Kjeldahl) |
|---|---|---|
| Casein hydrolyzate | 52.8 | 0.45 |
| Permeate (F < 3000 Da) | 5.5 | 0.03 |
| Retenate (F > 3000 Da) | 242.0 | 3.29 |

Figure 6:
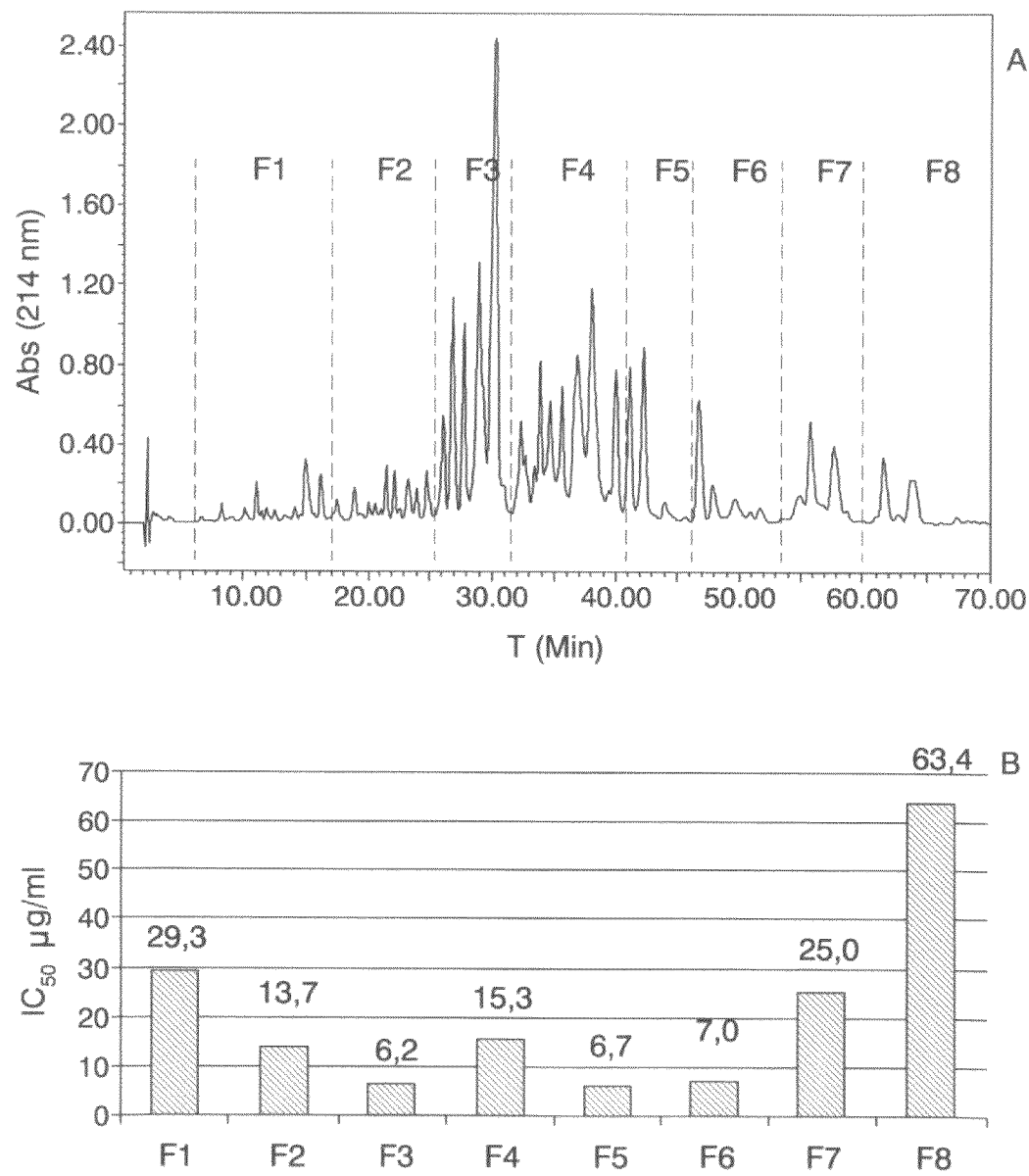

For the purpose of identifying the peptides responsible for the ACE-inhibitory and antihypertensive activity, following the ultrafiltering, the permeate was put through a separation process by RP-HPLC on a semi-preparatory scale in which 8 fractions were collected. Following the evaporation of the acetonitrile, these chromatographic fractions were freeze-dried and the ACE-inhibitory activity and the protein content were determined by means of the bicinchoninic acid method. FIG. 6 shows the chromatographic profile and the fractions obtained, as well as the ACE-inhibitory activity values, given as $IC_{50}$ for each one of the chromatographic fractions. The fractions termed F3, F5 and F6 in FIG. 6 are those displaying greater ACE-inhibitory activity, in other words, lower $IC_{50}$ values. These fractions were analyzed by RP-HPLC connected on-line to tandem mass spectrometry (RP-HPLC-MS/MS) using the methodology previously described. The major peptides identified are shown in Table 5.

The major peptides obtained in these chromatographic fractions were chemically synthesized by the solid-phase Fmoc method and their purity verified by RP-HPLC-MS/MS. The ACE-inhibitory activity of the chemically synthesized peptides, specifically of sequences SEQ. ID No. 12, SEQ. ID. No. 13 and SEQ. ID. No. 14, was determined. The activity results, given as $IC_{50}$, or protein concentration necessary to inhibit the ACE activity by 50%, are shown in Table 6. At least two of the three major peptides identified displayed potent ACE-inhibitory activity.

TABLE 7

ACE-inhibitory activity of the synthetic peptides identified in the fractions

| Sequence No. | Amino acids | $CI_{50}$ |
|---|---|---|
| SEQ. ID. No. 12 | RYLGY | Nd |
| SEQ. ID. No. 13 | AYFYPEL | 7.5 |
| SEQ. ID. No. 14 | HLPLPLL | 34.2 |

Example 6

ACE-Inhibitory and Antihypertensive Activity of the Peptides After Simulating Gastrointestinal Digestion of the Fragments Obtained by Hydrolysis of $\alpha_{s2}$-Casein PYVRYL SEQ. ID. No. 7.

The PYVRYL SEQ. ID. No. 7 peptide which had previously been identified in the $\alpha_{s2}$-casein hydrolyzates and was chemically synthesized and put through a two-stage hydrolysis process simulating gastrointestinal digestion (Alting, A. C., Meijer, R. J. G. M., Van Beresteijn, E. C. H. Incomplete elimination of the ABBOS epitope of bovine serum albumin under simulated gastrointestinal conditions of infants. Diabetes Care, 1997, 20:875-880). For this purpose, aqueous solutions of the synthetic peptides (10 mg/ml) are hydrolyzed, first with pepsin (E.C. 3.4.4.1, 570 U/mg protein) (Sigma) (enzyme-substrate ratio, 1:50, p/p) at pH 2.0 and 37° C. for 90 minutes and afterward with Corolase PP® (enzyme-substrate ratio 1:25, p/p) (Röhm, Darmstadt, Germany) at pH 7-8 and 37° C. for 2.5 hours. The reaction is interrupted by heating at 95° C. for 10 minutes in a water bath.

FIG. 7 shows that the PYVRYL peptide SEQ. ID. No. 7 hydrolyzes completely after incubation with pepsin and Corolase PP®. The main resulting fragment identified by RP-HPLC-MS/MS is the tripeptide PVY SEQ. ID. No. 15. This peptide was chemically synthesized and its ACE-inhibi-

TABLE 6

Major active peptides identified in fractions F3, F5 and F6 obtained from the permeate of the bovine casein pepsin-hydrolyzed for 3 hours.

| Subfr. No. | Exp. Mass | Theor. mass | Protein | Protein | Amino acids | Sequence No. |
|---|---|---|---|---|---|---|
| FC3 | 670.5 | 670.35 | $a_{s1}$-casein | 90-94 | RYLGY | SEQ. ID. No. 12 |
| FC5 | 901.5 | 901.43 | $a_{s1}$-casein | 143-149 | AYFYPEL | SEQ. ID. No. 13 |
| FC6 | 801.6 | 801.52 | B-casein | 134-140 | HLPLPLL | SEQ. ID. No. 14 | tory activity determined, a IC$_{50}$ value of 741.3 μM, in other words, 370 times less ACE-inhibitory activity than the starting peptide, was obtained. The antihypertensive activity of this tripeptide PVY SEQ. ID. No. 15 was determined by way of the administration thereof to SHR. The peptides are dissolved in distilled water and the corresponding dose administered to each rat in a volume of 1 ml. FIG. 8 shows the lowering of the SBP and DBP found in SHR rats at different points in time following the administration of PYV SEQ. ID. No. 15 at a dose of 2 mg/kg and of the PYVRYL peptide SEQ. ID No. 7 at a dose of 3 mg/kg, where it is shown that the administration of both of these peptides causes a significant lowering of the SBP and DBP of these animals. While the peak effect on the SBP of the PYV SEQ. ID. No. 15 occurs 2 hours following its administration, the peak effect of the PYVRYL peptide SEQ. ID. No. 7 does not take place until 4 hours following its administration. The faster onset of the antihypertensive effect in the case of the SEQ. ID. No. 15 could be due to the fact that when this sequence is administered, the enzymatic digestion process which must take place for it to be caused in vivo is obviated. These results demonstrate the antihypertensive activity of the SEQ. ID. No. 15 although, in principle, this cannot be attributed to its ACE-inhibitory activity. It is important to stress that, to date, the potent antihypertensive activity of the PYV peptide SEQ. ID. No. 15 had not be described until now.

Example 7

ACE-Inhibitory and Antihypertensive Activity of the Peptides after Simulating the Gastrointestinal Digestion of the Fragments Obtained by Hydrolysis of Complete Casein HLPLPLL SEQ. ID. No. 14.

The HLPLPLL peptide SEQ. ID. No. 14 which had previously been identified in the fraction having a molecular weight under 3000 Da of the total casein hydrolyzates and was chemically synthesized, was put through a two-stage hydrolysis process simulating gastrointestinal digestion (Alting, A. C., Meijer, R. J. G. M., Van Beresteijn, E. C. H. Incomplete elimination of the ABBOS epitope of bovine serum albumin under simulated gastrointestinal conditions of infants. Diabetes Care, 1997, 20:875-880). For this purpose, aqueous solutions of the synthetic peptides (10 mg/ml) are hydrolyzed, first with pepsin (E.C. 3.4.4.1, 570 U/mg protein) (Sigma) (enzyme-substrate ratio, 1:50, p/p) at pH 2.0 and 37° C. for 90 minutes and afterward with Corolase PP® (enzyme-substrate ratio 1:25, p/p) (Röhm, Darmstadt, Germany) at pH 7-8 and 37° C. for 2.5 hours. The reaction is interrupted by heating at 95° C. for 10 minutes in a water bath.

FIG. 9 shows the peptides that are obtained following the hydrolysis of the HLPLPLL peptide SEQ. ID. No. 14 identified by means of RP-HPLC-MS/MS which correspond to the HLPLPL hexapeptide SEQ. ID. No. 16 and the HLPLP pentapeptide SEQ. ID. No. 17. The HLPLPL SEQ. ID. No. 16 is an intermediate fragment, while the pentapeptide HLPLP SEQ. ID. No. 17 is resistant to the action of the gastrointestinal enzymes and is probably the end proteolysis product of the HLPLPLL peptide SEQ. ID. No. 14. The ACE-inhibitory activity of the HLPLP pentapeptide SEQ. ID. No. 17 was assayed and found to be a IC$_{50}$ value of 21 μM. Similarly, the antihypertensive activity in SHR of the final peptide resulting from the hydrolysis HLPLP SEQ. ID. No. 17 when a dose of 7 mg/kg is administered was determined. The lowering of the SBP and DBP are shown in FIG. 10. A significant lowering of the SBP and DBP is found in these animals, but in this case, the antihypertensive effect can indeed be attributed, at least in part, to its ACE-inhibitory activity.

The invention claimed is:

1. An isolated bioactive peptide wherein said peptide:
   a. has Angiotensin-Converting-Enzyme (ACE)-inhibitory activity in vitro and/or antihypertensive activity in vivo and/or antioxidant activity,
   b. is present in pepsin-hydrolyzed milk casein enzyme hydrolyzates, and
   c. comprises a first tyrosine residue at the second position from the N-terminus and a second tyrosine residue at the fourth or fifth position from the N-terminus, and at least two hydrophobic amino acid residues in the C-terminal tripeptide sequence selected from the group consisting of proline, leucine and tyrosine; and
   d. wherein said peptide has the amino acid sequence of SEQ ID NO. 12 or, and SEQ ID NO: 13.

2. The isolated bioactive peptide according to claim 1, wherein said peptide is derived from $\alpha_{s2}$-casein.

3. The isolated bioactive peptide according to claim 1, wherein said peptide is derived from $\alpha_{s1}$-casein.

4. The isolated bioactive peptide according to claim 1, wherein said peptide has ACE-inhibitory activity in vitro.

5. The isolated bioactive peptide according to claim 1, wherein said peptide has antihypertensive activity.

6. The isolated bioactive peptide according to claim 1, wherein said peptide has antioxidant activity by oxygen radical chelation.

7. The isolated bioactive peptide according to claim 1, wherein said peptide is obtained by a chemical or enzymatic synthesis method or by a recombinant method.

8. The isolated bioactive peptide according to claim 7, wherein said peptide is obtained by enzymatic hydrolysis of $\alpha_{s1}$-casein, or $\alpha_{s2}$-casein.

9. An isolated bioactive product comprising, an enzymatic hydrolyzate, a fraction thereof or a purification of thereof, containing the isolated bioactive peptide of claim 1.

10. The isolated bioactive peptide according to claim 1, wherein the bioactive peptide has a leucine at the first or third position of the C-terminal tripeptide sequence.

11. The isolated bioactive peptide according to claim 1, wherein the bioactive peptide has a tyrosine at first position of the C-terminal tripeptide sequence and has the amino acid sequence of SEQ ID NO: 12.

12. The isolated bioactive peptide according to claim 1, wherein the bioactive peptide has a proline at the third position of the C-terminal tripeptide sequence and has the amino acid sequence of SEQ ID NO: 13.

13. A method for producing the isolated bioactive peptide according to claim 1, wherein said method comprises
   dissolving or dispersing casein or whole milk in water or a buffer solution to obtain a mixture;
   optionally adjusting the mixture to a desired pH;
   adding a proteolytic enzyme or proteolytic microorganism capable of digesting protein present in the casein or whole milk to the mixture; and
   reacting the proteolytic enzyme or proteolytic microorganism with the protein for 10 minutes to 24 hours to obtain an isolated bioactive peptide according to claim 1.

14. The method of claim 13, wherein said method comprises
   adjusting the mixture to a pH of 3.0,
   reacting the proteolytic enzyme with the protein for 30 minutes to 3 hours,
   wherein the proteolytic enzyme is pepsin which is added to the mixture at an enzyme-protein ratio.

* * * * *